(12) United States Patent
Miller et al.

(10) Patent No.: US 10,018,462 B2
(45) Date of Patent: Jul. 10, 2018

(54) APPARATUS FOR DETERMINING GAUGE PROFILE FOR FLAT ROLLED MATERIAL

(71) Applicants: Jason Miller, Ada, MI (US); Nicholas D Carlevaris-Bianco, Midland, MI (US); Haley Nghiem, Holland, MI (US); Eric Twiest, Grand Rapids, MI (US); Amber Woods, Holland, MI (US); Brandon Wright, Belleville, MI (US); Cato Clemens, Grand Haven, MI (US); Han Huynh, Zeeland, MI (US); Steve Michel, Novi, MI (US); Lindsey Brown, Grand Rapids, MI (US); Britt Adamczyk, Grandville, MI (US)

(72) Inventors: Jason Miller, Ada, MI (US); Nicholas D Carlevaris-Bianco, Midland, MI (US); Haley Nghiem, Holland, MI (US); Eric Twiest, Grand Rapids, MI (US); Amber Woods, Holland, MI (US); Brandon Wright, Belleville, MI (US); Cato Clemens, Grand Haven, MI (US); Han Huynh, Zeeland, MI (US); Steve Michel, Novi, MI (US); Lindsey Brown, Grand Rapids, MI (US); Britt Adamczyk, Grandville, MI (US)

(73) Assignee: The Mill Steel Co., Grand Rapids, MI (US)

(*) Notice: Subject to any disclaimer, the term of this patent is extended or adjusted under 35 U.S.C. 154(b) by 0 days.

(21) Appl. No.: 14/737,893

(22) Filed: Jun. 12, 2015

(65) Prior Publication Data
US 2015/0276682 A1 Oct. 1, 2015

Related U.S. Application Data

(63) Continuation of application No. 13/226,107, filed on Sep. 6, 2011, now abandoned, which is a continuation (Continued)

(51) Int. Cl.
*G01B 11/06* (2006.01)
*G01N 29/07* (2006.01)
(Continued)

(52) U.S. Cl.
CPC .............. *G01B 11/06* (2013.01); *G01B 17/02* (2013.01); *G01N 29/04* (2013.01); *G01N 29/07* (2013.01); *G01N 2291/0234* (2013.01)

(58) Field of Classification Search
CPC ...... G01N 29/00; G01N 29/04; G01N 29/043; G01N 29/06; G01N 29/0654;
(Continued)

(56) References Cited

U.S. PATENT DOCUMENTS 2,356,660 A 8/1944 Deuel
2,935,680 A 5/1960 Bendix
(Continued)

*Primary Examiner* — Peter MacChiarolo
*Assistant Examiner* — Nathaniel Kolb
(74) *Attorney, Agent, or Firm* — Varnum, Riddering, Schmidt & Howlett LLP

(57) ABSTRACT

A gauge profile apparatus (100) includes a gauge profile system (104) and a lap count system (106) for determining an average three-dimensional profile over the length of a sheet coil (10). The gauge profile system (104) includes a lap profile measuring device (112) which will make a distance determination between top and bottom surfaces for the sheet coil (10). The lap count system (106) includes a distance sensor (288) and camera (290) for determining the average thickness of the sheet coil (10). A second embodiment of the gauge profile system (400) is also provided, which utilizes a PDA (404), an ultrasonic tester (406) and a string encoder (432).

1 Claim, 39 Drawing Sheets

Related U.S. Application Data of application No. 12/672,050, filed as application No. PCT/US2008/009364 on Aug. 4, 2008, now abandoned.

(60) Provisional application No. 60/963,221, filed on Aug. 3, 2007.

(51) Int. Cl.
 G01B 17/02 (2006.01)
 G01N 29/04 (2006.01)

(58) Field of Classification Search
 CPC .......... G01N 29/0663; G01N 29/0672; G01N 29/0681; G01N 29/069; G01N 29/07; G01N 29/075; G01N 29/22–29/02; G01N 29/2406–29/2493; G01B 11/06; G01B 17/02
 USPC .................. 702/155, 159, 171; 73/632–641
 See application file for complete search history.

(56) References Cited

U.S. PATENT DOCUMENTS

| | | | | |
|---|---|---|---|---|
| 3,835,306 A | * | 9/1974 | Bills | G06M 9/00 235/98 C |
| 4,232,218 A | * | 11/1980 | Kenton | G06M 9/00 377/53 |
| 4,301,366 A | | 11/1981 | Bertin | |
| 4,542,297 A | | 9/1985 | Hold | |
| 4,669,310 A | * | 6/1987 | Lester | G01B 17/025 73/1.81 |
| 4,789,431 A | | 12/1988 | Typpo | |
| 5,299,458 A | * | 4/1994 | Clark, Jr. | G01N 29/07 73/597 |
| 5,428,557 A | * | 6/1995 | Harbaugh | G06M 9/00 377/28 |
| 7,116,428 B2 | * | 10/2006 | Sauerland | G01B 11/0691 356/502 |
| 2005/0162662 A1 | * | 7/2005 | Sauerland | G01B 11/0691 356/502 |
| 2013/0050681 A1 | * | 2/2013 | Miller | G01B 11/00 356/72 |

* cited by examiner

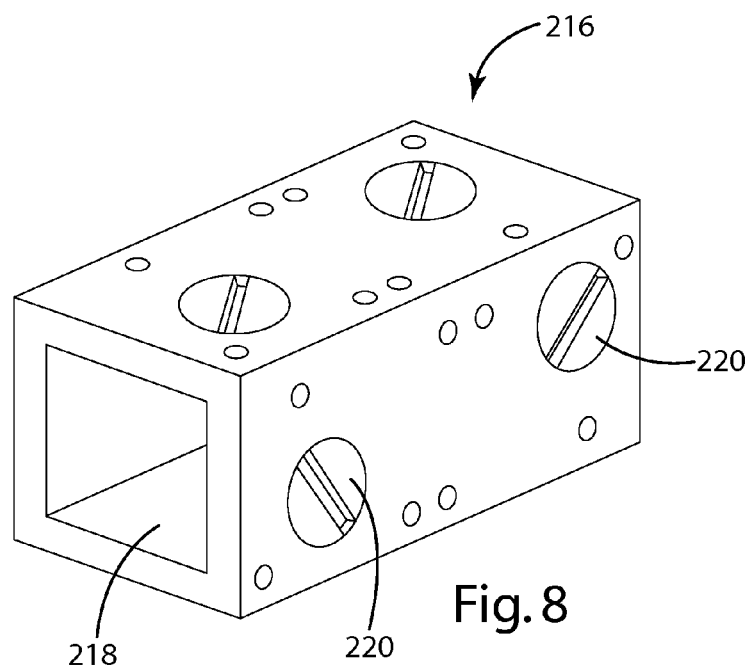
Fig. 8
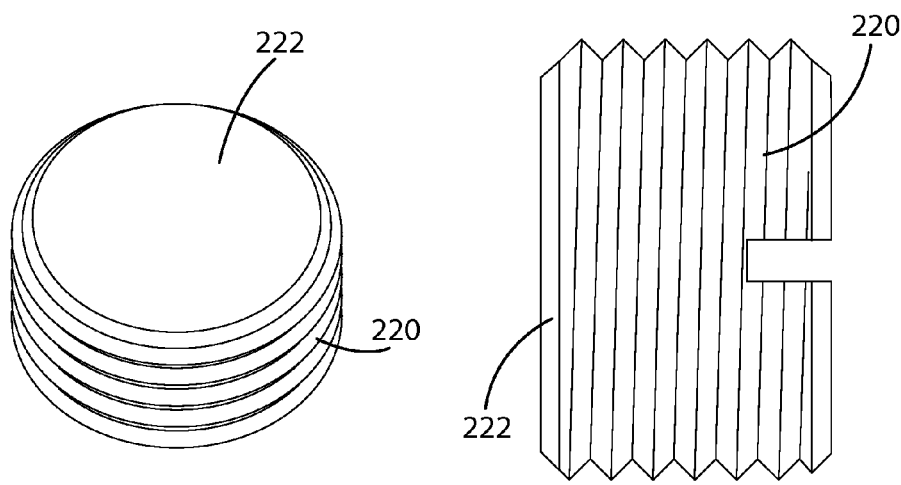
Fig. 9
Fig. 10

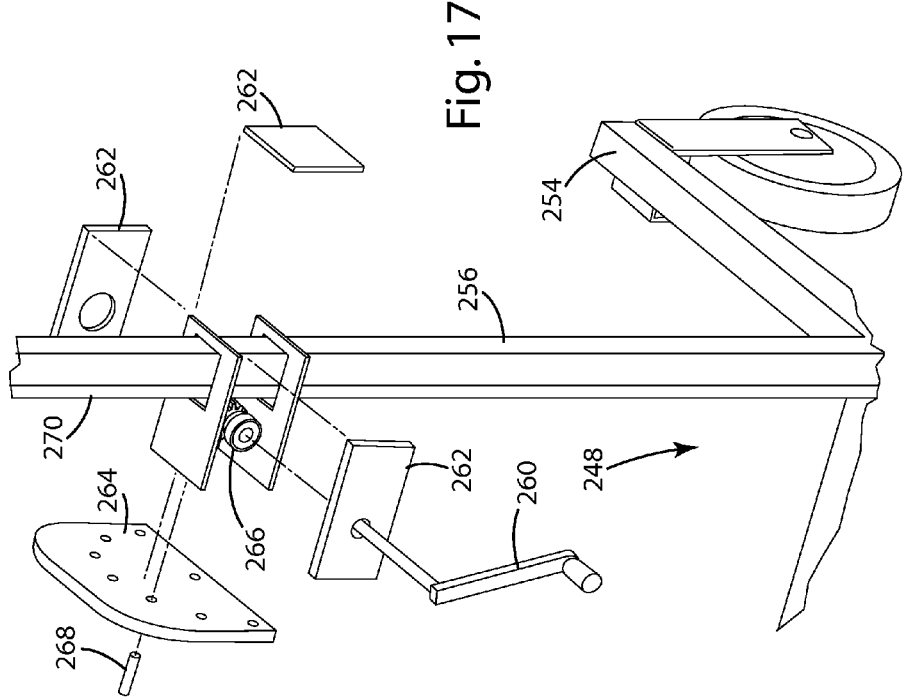
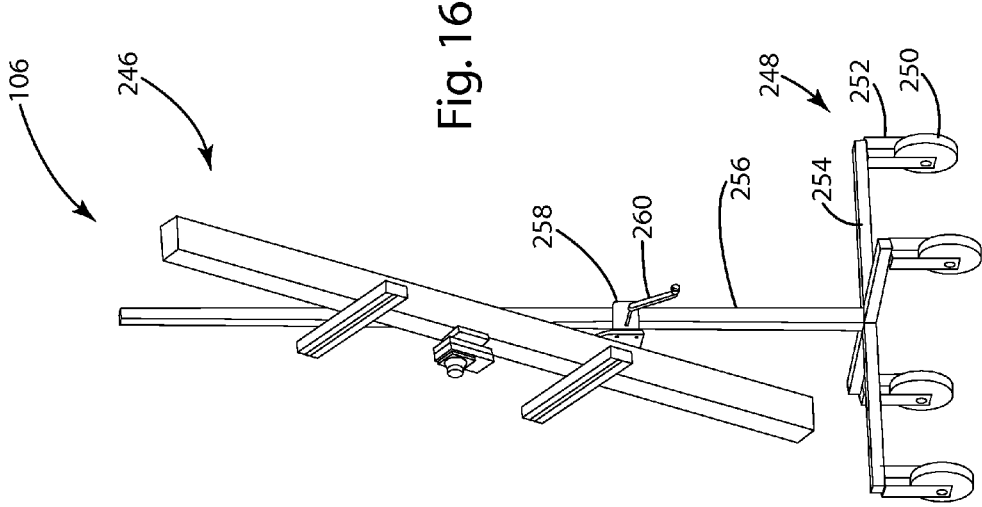

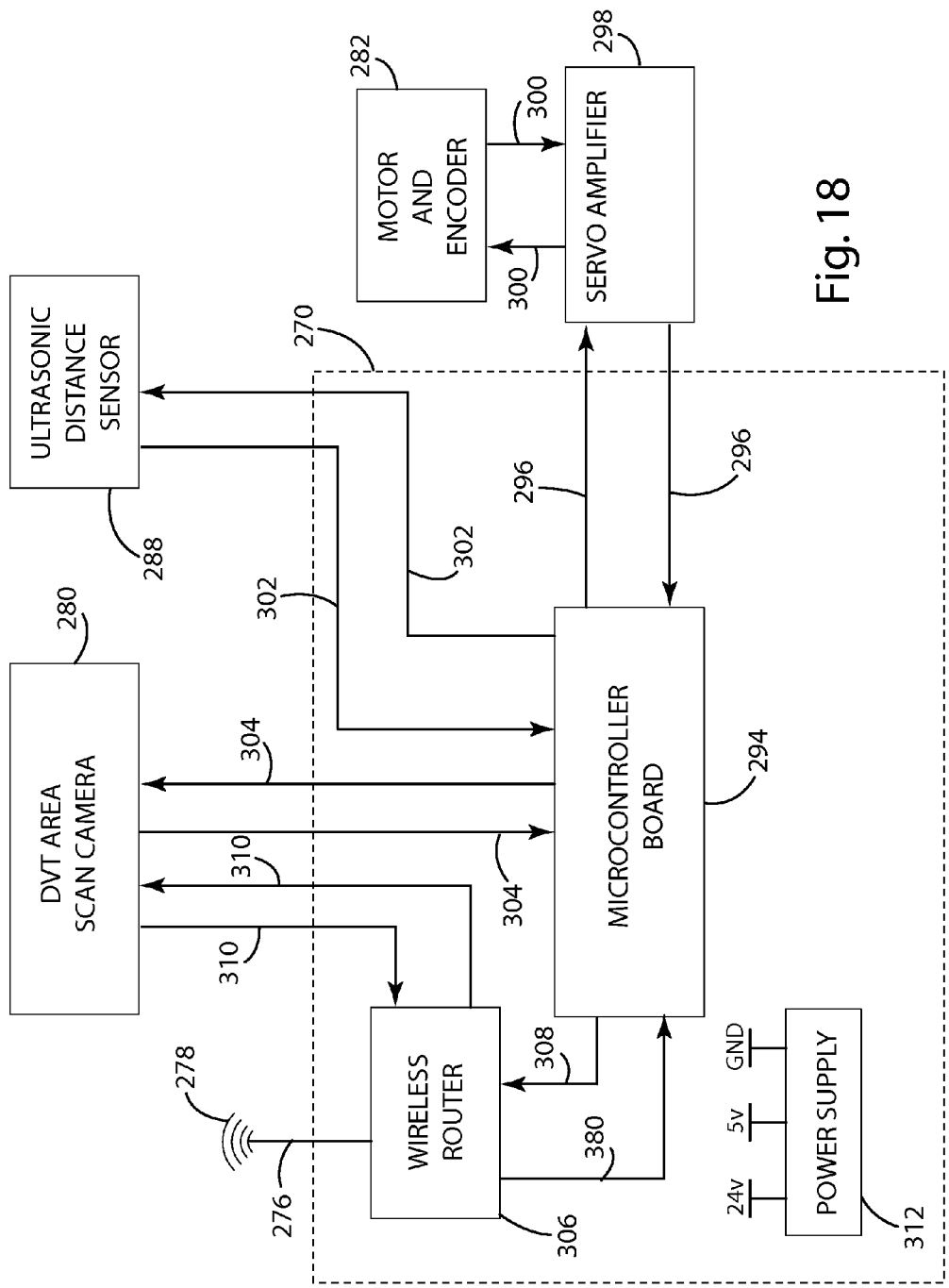

Partial Image Acquisition

Low Pass Filter to Reduce Noise

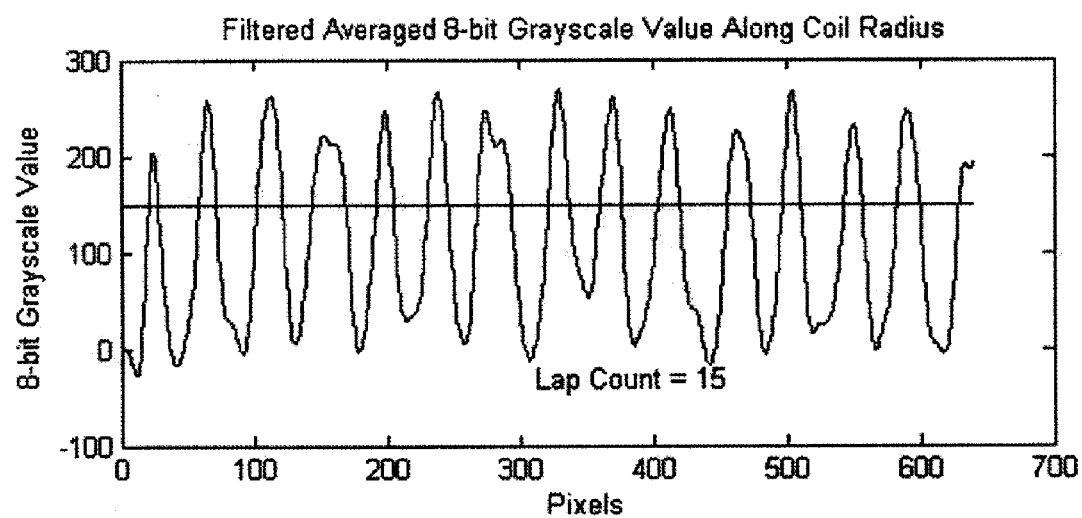
Filtered Data w/ Lap Count     Fig. 25
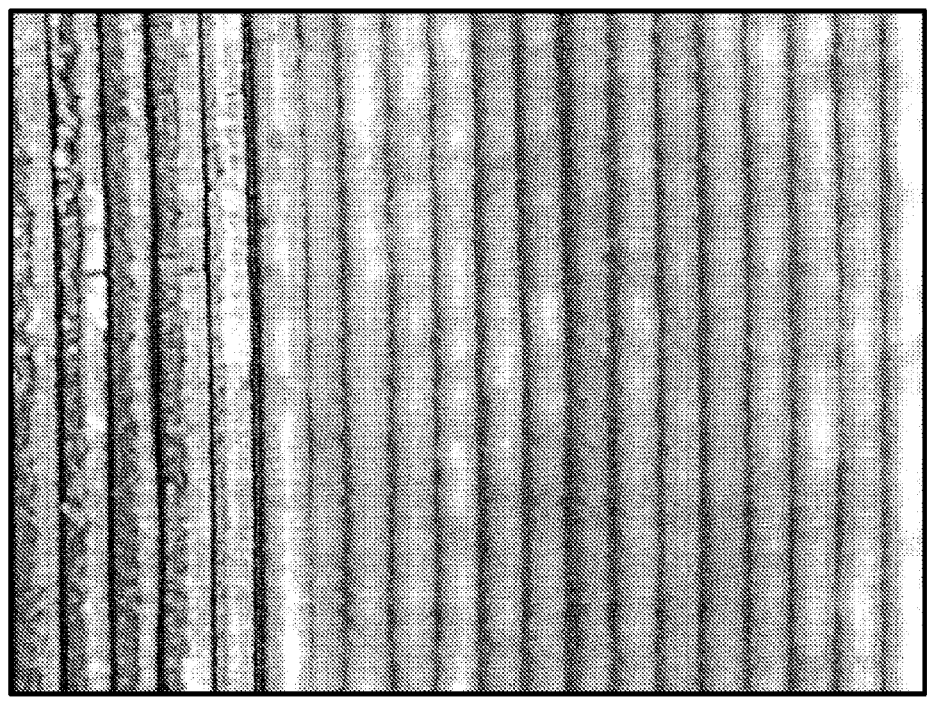
OUT OF FOCUS IMAGE     Fig. 26

"START" STATE FUNCTIONAL BLOCK DIAGRAM

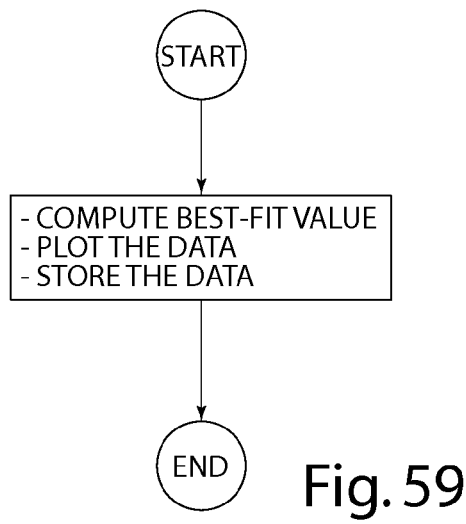

Fig. 59

"PROCESS THE COLLECTED DATA"
STATE FUNCTIONAL BLOCK DIAGRAM

CALCULATE THE CURVE-BEST-FIT EQUATION FOR THE COLLECTED DATA $$y = a + bx + cx^2$$

$$\begin{cases} \sum_{i=1}^{n} y_i = a \sum_{i=1}^{n} 1 + b \sum_{i=1}^{n} x_i + c \sum_{i=1}^{n} x_i^2 \\ \sum_{i=1}^{n} x_i y_i = a \sum_{i=1}^{n} x_i + b \sum_{i=1}^{n} x_i^2 + c \sum_{i=1}^{n} x_i^3 \\ \sum_{i=1}^{n} x_i^2 y_i = a \sum_{i=1}^{n} x_i^2 + b \sum_{i=1}^{n} x_i^3 + c \sum_{i=1}^{n} x_i^4 \end{cases}$$

$y_i$: THICKNESS READINGS
$x_i$: DISTANCE READINGS

Fig. 60

APPARATUS FOR DETERMINING GAUGE PROFILE FOR FLAT ROLLED MATERIAL

CROSS-REFERENCE TO RELATED APPLICATIONS

This application is a continuation of and claims priority of U.S. patent application Ser. No. 13/226,107 filed Sep. 6, 2011, which is a continuation of and claims priority of U.S. patent application Ser. No. 12/672,050 filed Feb. 3, 2010, which is a United States National Stage application under 35 U.S.C. §371 of International Patent Application Serial No. PCT/US08/009364 filed Aug. 4, 2008, with the international application claiming priority of U.S. Provisional Patent Application Ser. No. 60/963,221 filed Aug. 3, 2007.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

Field of the Invention

The invention relates to industrial measurement systems and, more particularly, to apparatus and methods for determining gauge profiles for rolled materials.

Background Art

Throughout relatively recent history, a substantial amount of development work has occurred with respect to apparatus and processes for manufacturing, forming and shaping various types of materials, including, for example, metallic materials. One such metallic material in worldwide use is steel. Steel has been used for a substantial part of relatively modern history. Steel is an alloy consisting mostly of iron, with a carbon content often within the range of 0.02% to 2.04% by weight, typically depending on grade. Although carbon is the most cost-effective alloying material for iron, various other elements may be used, such as manganese and tungsten. The carbon and other elements act as a hardening agent, preventing dislocations in the iron atom crystal lattice from sliding past one another. The amount of alloying elements and the form of their presence in the steel (e.g. solute element, precipitated phase) controls qualities such as the hardness, ductility and tensile strength of the resulting steel.

Long before even the Renaissance, steel was produced by various and what may be characterized as "inefficient" methods. However, steel use became more common after more efficient production methods were devised in the 17th Century. With the invention of the Bessemer process in the mid-19th century, steel became what was then a relatively inexpensive mass-produced good. Further refinements in the process (e.g. basic oxygen steel making) lowered cost of production, while increasing metal quality. Today, modern steel is generally identified by various grades of steel defined by various standards organizations.

Today, steel and other materials are produced and generated through various apparatus so as to obtain differing sizes and shapes of the resultant products. For example, one known method for forming and shaping steel utilizes a process known as "continuous casting." This process involves the pouring of liquid steel directly into semi-finished shapes, such as slabs, blooms, blanks, or billets. The continuous casting process typically produces a slab of steel having certain ranges of pigments and width. These slabs are often cut into pieces of varying lengths, dependent upon commercial particulars. In some instances, it is desired to produce a flat, rolled steel strip from such material. To produce such a rolled steel strip, a discreet slab can be reheated, and passed through one or more hot rolling mill-stands. Such hot rolling procedures can result in reducing the thickness to, for example, approximately 2.5 millimeters. To obtain further reductions in thicknesses, the materials resulting from the hot rolling process can be passed through one or more reducing/finishing cold rolling millstands.

Other advancements in technologies associated with the rolling of metallic stock (such as stripped steel or the like) have been made during the last several decades. These advances have applied not only to steel, but to other types of metals. In fact, a substantial amount of research and development has occurred during the past several years with respect to the rolling of non-metallic products, such as plastics and the like.

In the rolling of material stock, such as steel, a problem has existed with respect to maintaining a uniform gauge or thickness of the material during the rolling process. Correspondingly, this problem has also been presented with respect to means for measuring the gauge or thickness after the rolling process has been completed. In this regard, it is particularly difficult to obtain gauge measurements when the steel or other materials are in a coiled configuration. For example, certain organizations may operate as steel service centers, which purchase coiled sheet steel from rolling mills. Such service centers may, for example, function so as to slit or otherwise process the coiled sheet material for customers, which may include stampers, roll formers and the like. In the past, it has been substantially difficult to obtain an accurate determination of coil thickness or, what may be characterized as a "gauge profile," prior to undertaking the slitting or other processes being performed by the service center. However, the slitting of the coiled sheet material cannot be undertaken until after there is a customer allocation for the service center. Accordingly, the service center cannot obtain an accurate gauge profile until after such customer allocation are exposed to substantial monetary risks due to an inability to accurately determine coil thickness prior to processing. These risks are comprised of losses through devalued material, lost machine time, lost freight, customer downtime and subsequent effects.

Various systems have been developed and are known in the prior art which are directed to material gauge measurements and facilitating the accuracy thereof.

For example, Hold, U.S. Pat. No. 4,542,297 issued Sep. 17, 1985, discloses an apparatus for measuring a thickness profile of steel strip. The apparatus includes a radiation source which is reciprocally movable in a stepwise fashion across the strip width on one side thereof. A single, elongated detector on the other side of the strip is aligned with the scanning source. This detector may be a fluorescent scintillator responsive to the incident radiation. In turn, the incident radiation is dependent on the degree of absorption by the strip.

In addition to the foregoing, Hold discloses apparatus for sensing the degree of excitation in the detector, with the sensing occurring in synchronism with the scanning source. This combination is used to provide an output which is considered to be representative of the thickness profile of the steel strip. The profile is then displayed on a television screen. A thickness gauge (disclosed as being "conventional" by Hold), which may involve x-ray technology, is used in conjunction with the profile gauge, so as to compensate the output of the profile gauge for any variations in the strip thickness along the length of the coil.

Hold further describes the concept that the current market for hot rolled strip (with the term "strip" being described by Hold as including "sheet" and "plate" steel) requires a relatively smooth and cigar-shaped profile. Hold states that desired profiles have less than 5 microns edge-to-edge thickness differential. In addition, Hold also states that the "crown" should be less than 70 microns. The crown is defined as being the difference between the thickness at the edges of the strip and the center thickness of the strip. It should be noted that Hold is describing thickness measurements occurring as the strip is being rolled.

Hold further describes the concept that the measurement information has previously been obtained off-line from contact measurements. However, such off-line measurements only provide what are considered to be "historical" measurements. Prior systems have been used which can be characterized as being "on-line" through the use of a scanning mechanism providing a relatively rapid read-out. In this manner, Hold describes the concept that relatively rapid corrective action may be taken. With the on-line system, measurements are taken across the width by combining the physical traverse of a single radiation source and an associated detector on two limbs of what is characterized as a "C"-frame across the strip. Alternatively, a physical traverse of a single radiation source may be made across the strip with a series of fixed detectors on the other limb, or a series of fixed sources with equal or different fixed detectors. Hold states that movement of the frame is relatively cumbersome, slow and energy consuming. Alternative movements of individual source/detector apparatus in synchronism is characterized by Hold as being relatively complex. Also, with two moving mechanisms, wear and inertia are considered problems. In an embodiment using a series of fixed detectors, measurements can be made only at a number of discrete points, and difficulties may arise in "collection" of the data from these detectors, as well as ensuring that each detector responds to radiation incident only on itself and not on adjacent detectors.

In Hold, the radiation source is a radio-isotope (which may be Americium 241) which is driven across the strip width and relatively rapid discrete steps by a pulsed "stepper" motor. Further, a linear array of such sources is disclosed, disposed in the direction of the travel of the strip for purposes of enhancing the output.

The detector is considered to be continuous in the sense that it is a single integrated unit. As earlier described, the unit may be a fluorescent plastic scintillator, with a massive number of scintillation particles being embedded in a plastic matrix. Light output from these particles is collected by photomultipliers mounted on each end of the plastic rod. The edge of the strip, utilized as the datum for the trace, is identified by an instantaneous change in the amount of radiation incident on the scintillator, as the source transverses the strip edge. The time-base for the trace (i.e. the x-coordinate) is considered to be governed by the stepper motor at each step, so as to effect the reciprocating scan across the strip.

In brief summary, Hold discloses an apparatus for measuring profile thickness which utilizes a radiation source and detector in order to determine the strip profile. This apparatus essentially does a "head-to-tail" representation, by performing linear gamma inspection across the face of the strip at multiple points. It should be noted that Hold requires that the steel strip not be in an coil form. Instead, if the strip had been coiled, the coil needs to be opened up and traverse the measuring apparatus, in order to gather the requisite information.

A relatively earlier apparatus for measuring thickness of sheet metal and the like is disclosed in Bendix, et al., U.S. Pat. No. 2,935,680 issued May 3, 1960. The Bendix device is specifically directed to gauging the thickness of sheets of magnetizable metal. The apparatus includes two equivalent electromagnets, each having a central core and a surrounding pole. A coil is supported on each core, with a common alternating current source for the coils. The source is sufficient so as to cause the sheets under test to be magnetically saturated by the electromagnets during at least a portion of the alternating current cycle. The core and the pole of the first magnet are bridged by a reference sheet of metal, and the core and pole of the second magnet are bridged by the sheet of metal under test. Branch resistance circuits are connected to the alternating source on opposite sides of the coils, and an adjustable resistance unit is connected to the resistance circuits. The adjustable resistance unit is connected to the alternating current source intermediate the coils, and a means for indicating measurements is positioned in series with the adjustable unit.

In summary, the apparatus disclosed in Bendix, et al. uses an alternating current, and a process which induces and measures the magnetic field around a charged sheet as the sheet flows into a die. The apparatus essentially measures the timing required for the entering material to become magnetically saturated. The timing is then translated into a thickness measurement. Again, Bendix, et al. requires any material under test to be unrolled and to enter the measurement system one layer or one sheet at a time. Also, it is obvious that in view of their required magnetic characteristics, the Bendix, et al. system is limited to measurement of ferrous materials.

Bertin, et al., U.S. Pat. No. 4,301,366 issued Nov. 17, 1981 discloses an apparatus and processes for measuring strip thicknesses in a material strip generated as an output from a mill. A radiation source and detector are positioned at a gauging station, with the stream of material moving pass the station. As the material moves pass the station, an electrical signal is generated which varies as a function of the material at the station. The signal includes a lower frequency component, higher frequency cyclical component and higher frequency noise component. A circuit for providing a thickness output varying as a function of the lower frequency component of the signal, and a circuit providing an output indicating chatter varying as a function of the higher frequency cyclical component, are utilized. Bertin, et al. also disclose apparatus for providing both digital and analog versions of their system.

In general, Bertin, et al. disclose an apparatus and methods for detecting "chatter" in systems directed to thickness measuring of strip products. More specifically, in processes such as the cold rolling of steel, there may be relatively prolonged regions of high frequency variations in the product. An example is a thickness variation, which is commonly referred to as chatter. A relatively common cause of chatter is a mechanical resonance in the rolling mill, which tends to make the rolls "bounce." This activity gives rise to a thick (or thin) spot in the steel strip for each bounce. These thickness variations can be considered to be quality defects. More specifically, a primary purpose of the Bertin, et al. system is to collect thickness information so as to detect signs of chatter. The chatter can be characterized as a symptom of the harmonic bouncing of the gauge-reducing rollers which show up in the material as cyclical thickness variations across the length of the material strip. As with certain of the aforedescribed references, the Bertin, et al. apparatus cannot be utilized with material strips, while the strips are in coil form. Also, it appears that Bertin, et al. require that the material strip be in motion relative to the gauging or chatter measuring station.

Another relatively early disclosure of an apparatus and method for determining average thicknesses of metallic strip materials from rolling mills is set forth in Deul, Jr., et al., U.S. Pat. No. 2,356,660 issued Aug. 22, 1944. The patent describes the concept that in the rolling of metallic stock, such as strip steel, it is a problem to measure the thickness of the material during the rolling process, and to obtain some means of determining the thickness throughout the entire width of the traveling strip material. The disclosed measuring apparatus is used while the strip material is being coiled on a reel. A radial reel zone is provided, with a counting apparatus for determining the number of revolutions of the reel corresponding with the predetermined radial thickness of the coil strip defined by the entry and exit of the outer face of the coiled strip on the reel. A synchronistic control is utilized with the counting apparatus which includes an actuating member driven in synchronistic relationship with the reel. Mechanical clutching devices are utilized intermediate the rotatable coil winding reel and the revolution counter, and control apparatus are utilized for synchronizing the starting and stopping of the counting mechanism. The automated control apparatus includes photo-electric control devices, with a series of light beams being generated coincident with the strip surface at the beginning of the radial zone. A second beam is disposed so as to be coincident with the strip surface at the ending of the radial zone. In general, the Deul, Jr. et al. patent reference discloses a method for calculating the average thickness of coiled materials by measuring the elevation of the coil from the mandrel that the materials are being spooled onto, and dividing this measurement by the number of laps. As with other known systems, the Deul, Jr., et al. system is not utilized with the material while it is in coil form, but instead it counts the number of turns a device makes in the coiling process, thus requiring motion. Also, this system essentially "assumes" that the cross section of the coil material is a true rectangle. That is, the system does not take into account the commonly known edge-crown-edge profile which results during manufacture of various types of rolled material strips.

As previously described herein, a number of the known, prior art systems for measuring material strip thicknesses must be utilized while the strip is in an "unrolled" or "uncoiled" state. However, as also previously described, for companies such as steel service centers which purchase sheet steel in coiled states, it has been extremely difficult to determine strip gauge. To date, certain processes for estimating gauge ranges are known for use with coils consisting of sheet steel or the like. Some of the known gauge range estimates are created from measurements which consist of the highest and lowest micrometer/caliper readings which are typically taken during a receiving process for the coils on the production floor. Unfortunately, the only portions of the incoming coil which are accessible for purposes of taking these readings essentially comprise the edges and the outside/inside laps of the coil. These areas are inherently considered to be the most erratic and least "representative" areas of the coil. For example, edges of coils typically have a "feather" affect and provide relatively low thickness measurements. Correspondingly, heads and tails of coils are typically high and provide relatively large thickness measurements. These circumstances result in the generation of unreliable data. It is apparent that such unreliable data can result in attempts to apply coils improperly to customer orders.

BRIEF DESCRIPTION OF THE SEVERAL VIEWS OF THE DRAWING

The invention will now be described with reference to the drawings, in which:

FIG. 8 illustrates a bearing compartment which maybe utilized as part of an ultrasonic thickness sensor for the gauge profile system in accordance with the invention;

FIG. 9 is a perspective view of a plug bearing which may be utilized with the bearing compartment illustrated in FIG. 8;

FIG. 10 is a vertical cross section of the bearing plug illustrated in FIG. 9;

FIG. 16 is a partially perspective view of a stand which may be utilized with a lap count system which, in turn, may be utilized with the gauge profile apparatus in accordance with the invention;

FIG. 17 is a partially perspective and exploded view of the stand illustrated in FIG. 16;

FIG. 18 is a partially diagrammatic and partially functional block diagram of the control system for the lap count system in accordance with the invention;

FIG. 25 is an illustration of averaged grayscale values similar to FIG. 23, but with the plot utilizing data filtered through the low pass filter with the characteristics illustrated in FIG. 24;

FIG. 26 is a photographic image showing a raw photograph of the coil laps taken through the use of the lap count system in accordance with the invention;

FIG. 59 is a state functional block diagram showing the "process the collected data" state; and FIG. 60 is an illustration of an example set of equations which may be utilized with "curve-best-fit" equations for the data collected.

DETAILED DESCRIPTION OF THE INVENTION

The principles of the invention will now be described with respect to a gauge profile apparatus 100 disclosed herein and primarily illustrated in FIGS. 3-28. The gauge profile apparatus 100 includes a gauge profile or cross-section profile system 104, and a lap count system 106. In addition to the gauge profile system 104, a second embodiment of a gauge profile system is also disclosed herein. The second embodiment is described herein as gauge profile system 400 and is illustrated in FIGS. 29-60. It should be emphasized that whether the lap count system 106 is used with the gauge profile system 104 or the gauge profile system 400, the resultant purposes for a gauge profile apparatus in accordance with the invention are the same. The gauge profile apparatus 100 is adapted to be used with flat rolled materials which have been formed into coils. The materials may be sheet steel, other types of metals or other types of materials (such as plastics or the like). The primary purpose of the gauge profile apparatus 100 is to project or otherwise "estimate" the gauge thickness at any point of a coil with a relatively high degree of accuracy. The resultant output from the gauge profile apparatus 100 can be characterized as a three dimensional ("3D") gauge projection.

Figure 1:
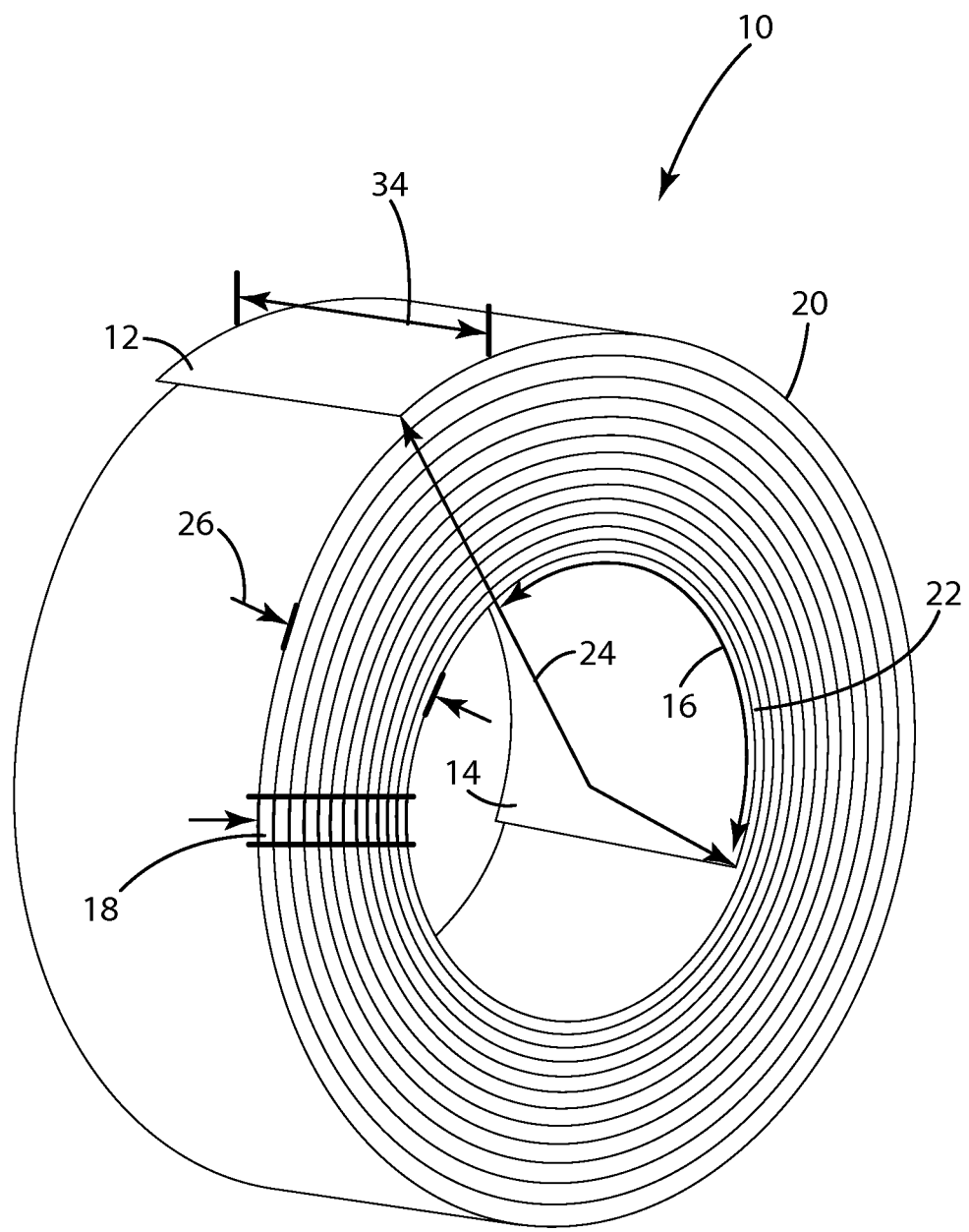
FIG. 1 is a perspective view of a sheet steel coil which may be utilized as a work piece under test with a gauge profile apparatus in accordance with the invention.

As previously described in the section entitled "Background Art," companies such as steel service centers purchased coiled sheet steel from various mills. Service centers, such as the assignee of the current invention, may undertake activities such as slitting the coiled sheet steel for use by various stampers and roll formers. As also earlier described, material can be compromised as a result of an inability to accurately determine coil thickness prior to slitting. Also, problems exist with respect to lost machine time, lost freight, customer downtime and the like. For purposes of describing concepts associated with determination of coil thicknesses, an example embodiment of a sheet coil 10 is illustrated in FIG. 1. A cross section of the sheet coil 10 is further illustrated in FIG. 2. As shown therein, the sheet coil 10 may consist of sheet steel or other materials, as previously described. Parameters associated with the sheet coil 10 are illustrated in FIG. 1, and include a series of laps 18. The outermost lap is shown as the outside lap 12 while the innermost lap is shown as inside lap 14. The difference in relative positions of the ends of the outside lap 12 and inside lap 14 is shown as the overlap length 16. The outermost diameter of the coil 10 is identified as the outside diameter 20, while FIG. 1 also illustrates the inside diameter 22. A lap count radius 24 is further shown in FIG. 1, and is defined as the radial length between the center point of the sheet coil 10 and the outside lap edge 12. In turn, the total coil thickness 26 is defined as the thickness of the total number of laps, as illustrated in FIG. 1.

Currently, gauge range estimates, when not provided by outside processors of the coiled sheet materials, are typically created from highest and lowest micrometer/caliper readings taken during the receiving process on the production floor. Unfortunately, however, and as apparent from the overall shape and configuration of the sheet coil 10 shown in FIG. 1, the only portions of the sheet coil 10 that are accessible for purposes of taking such readings are the edges, outside lap 12 and inside lap 14. However, these areas of the sheet coil 10 are known to be inherently the most erratic and least representative areas of the sheet coil 10. More specifically, the edges typically have what can be considered a "feather" effect and are relatively low. In contrast, the "heads" and "tails" of the sheet coil 10 are typically high. Such circumstances generate unreliable data which often results in an attempt to apply sheet coils improperly to customer orders.

Figure 2:
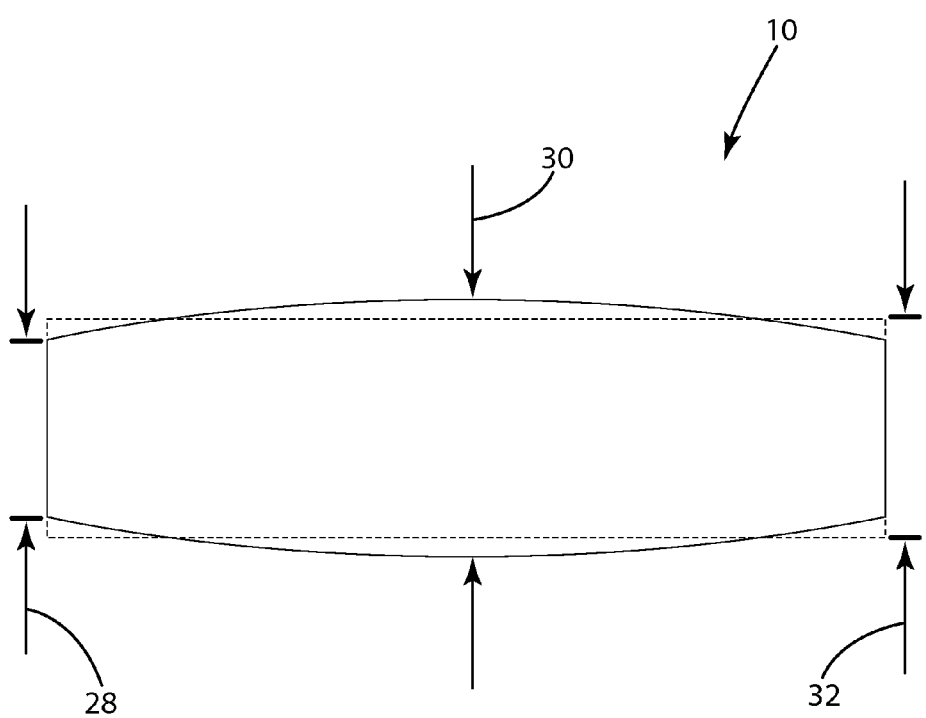
FIG. 2 is an illustration showing a cross section of a coil and the relationship between thicknesses of coil edges and the coil crown.

In this regard, it has been noted that rolls generated at steel mills and the like typically have a slightly concave shape for purposes of controlling the direction of slabs/coils, while performing gauge reduction. The result of the shape is a coil which would typically have the cross section of sheet coil 10 illustrated in FIG. 2. It should be emphasized that FIG. 2 is somewhat of an "exaggerated" cross section for purposes of description. As shown therein, the relative center of the sheet coil 10 has a thickness which is greater than the thickness which exists at its edges. For purposes of description, FIG. 2 illustrates the sheet coil 10 as having an edge gauge 28. The thickness portion 30 of the sheet coil 10 is at or near the center of the coil 10, and is typically referred to as the crown or crown gauge 30. The actual amount of crown will typically vary from mill to mill and, in fact, even coil to coil.

Notwithstanding the foregoing, it has been found that although the gauge of the sheet coil 10 can change from head to tail, the relative thickness between the edge gauges 28 and the crown gauge 30 will remain relatively constant. Accordingly, if the width, weight and length of the sheet coil 10 could be accurately determined, and a relatively accurate profile of the crown 30 could be ascertained, then the gauge at any point of the sheet coil 10 should possibly be able to be projected with a relatively high degree of accuracy.

Figure 3:
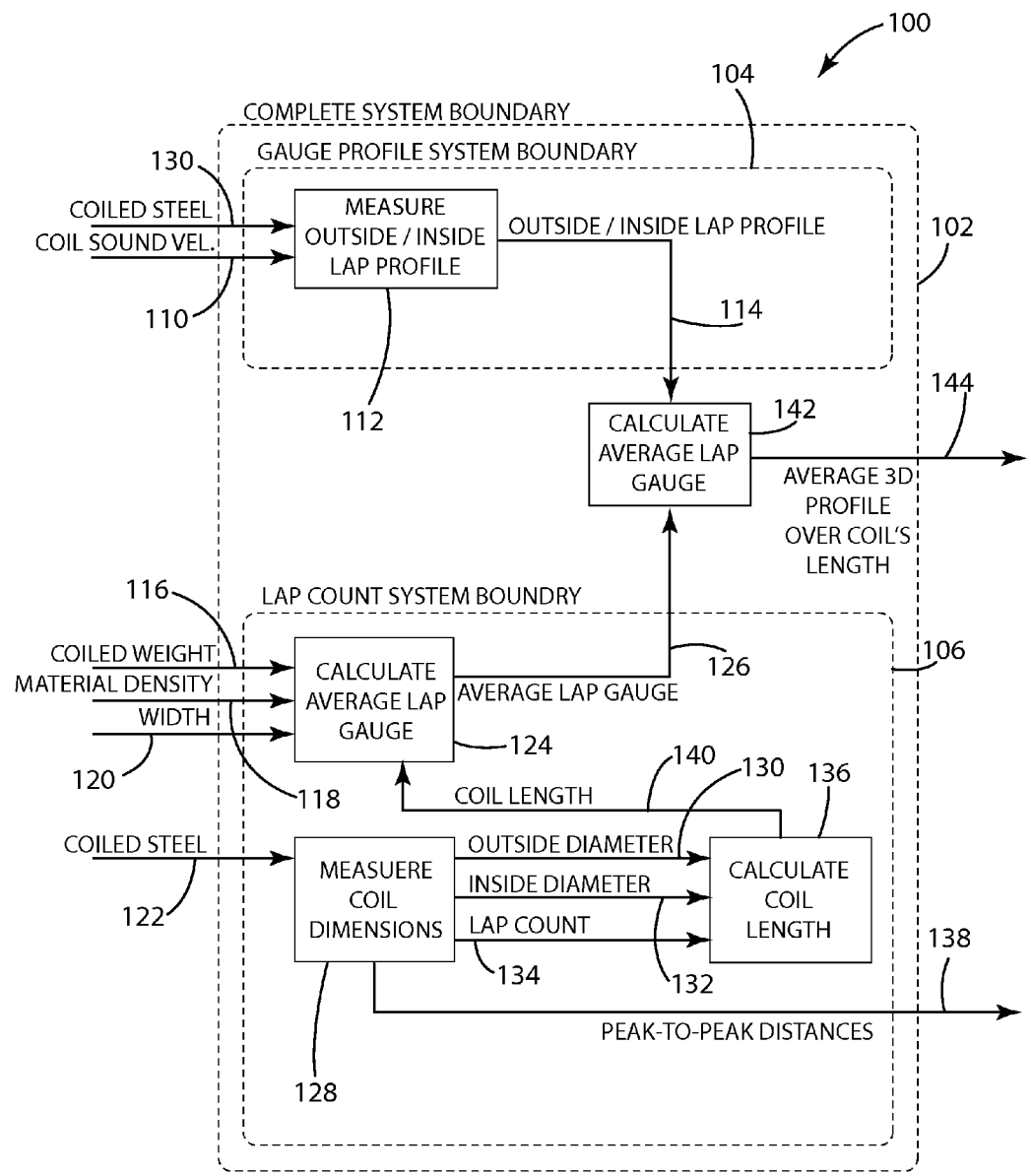
FIG. 3 is a partially diagrammatic and partially block diagram indicating the processes associated with the gauge profile apparatus in accordance with the invention, and the specific input and output parameters utilized by the apparatus in accordance with the invention.

FIG. 3 illustrates a partially symbolic and partially functional block diagram of the inputs, outputs and processes performed by the gauge profile apparatus 100. As previously stated, the ultimate output desired through the use of the gauge profile apparatus 100 in accordance with the invention is an average three-dimensional profile over the length of the sheet coil 10. Referring specifically to FIG. 3, the gauge profile apparatus 100 is shown as having a symbolic boundary 102. The apparatus 100 essentially comprises two main or primary systems; namely, a gauge profile or cross-section profile system 104 and a lap count system 106. The symbolic boundaries of the systems 104, 106 are illustrated in FIG. 3.

The gauge profile or cross section profile system 104 essentially determines the relative distribution of material of the sheet coil 10 for a cross section of the material. As will be described in subsequent paragraphs herein, and in accordance with one embodiment of the invention, the gauge profile system 400 utilizes an ultrasonic gauge device for bombarding the sheet coil material with high frequency sound waves. Accordingly, inputs for the gauge profile system 104 are symbolically illustrated in FIG. 3 as being the sheet coil 10 shown as input 108 and a determined coil sound velocity 110. The inputs 108, 110 are applied to a lap profile measuring device 112, which effectively measures the outside/inside lap profile. The lap profile measuring device 112 will essentially take the results of the bombardment of the sheet coil 10 with the high frequency sound waves, and translate the timing between the wave reflections or "echoes," into a distance determination between top and bottom surfaces for the sheet coil 10. As will be described in subsequent paragraphs herein, the lap profile measuring device 112 or calculations associated therewith are used in conjunction with a linear slide system which allows for the ultrasonic gauge measurement to traverse across the width (shown as width 34 in FIG. 1) of the sheet coil 10, while simultaneously capturing thickness measurements during traverse. The output of the lap profile measuring device 112 is therefore shown symbolically in FIG. 3 as the lap profile parameter 114.

As earlier stated, the gauge profile apparatus 100 also includes, in addition to the gauge profile system 104, a lap count system 106. The system 106, and the particular embodiment of the gauge profile apparatus 100 in accordance with the invention, comprises a system using a commercially available ultrasonic distance sensor and camera (with the camera having an internal processor) for purposes of determining the average thickness of the sheet coil 10. This determination is achieved through the counting of the exact number of laps of the sheet coil 10, as well as making a determination of the outside diameter of the sheet coil 10 and the inside diameter of the sheet coil 10. As will be made apparent from subsequent description herein, this information, combined with a measurement of the width 34 of the sheet coil 10, allows for the volume of the sheet coil 10 to be determined with a substantial amount of relative accuracy. With the volume combined with a weight measurement, a determination of the "average gauge" of the sheet coil 10 may be determined.

More specifically, and turning to FIG. 3, the illustration shows, somewhat symbolically and somewhat diagrammatically, an input to the lap count system 106 as comprising the coil weight 116. The coil weight 116 can be determined by any suitable and well known apparatus and procedures. In addition to the coil weight 116, the material density 118 and the width (shown symbolically in FIG. 3 as width 120) are applied as input parameters to a functional calculation which can be characterized as an average lap gauge calculator 124. The output of the average lap gauge calculator 124 is a representation of the average lap gauge, shown as lap gauge 126 on an output from the average lap gauge calculator 124.

In addition to the inputs consisting of the coil weight 116, material density 118 and width 120, the lap count system 106 also includes, as an input, the overall shape and configuration of the sheet coil 10. Through the use of the aforedescribed distance sensor and camera, coil dimensions can be obtained, through the devices shown in a symbolic format as the coil dimension calculator 128. Again, the calculator 128 is merely a symbolic representation and clearly includes input parameters coming from outputs of a distance sensor and camera.

The outputs of the coil dimension calculator 128 are illustrated as outputs 130, 132, 134 and 138. More specifically, output 130 represents a determination of the outside diameter (previously shown in FIG. 1 as outside diameter 20 of the sheet coil 10). The output 132 consist of the inside diameter (previously identified as the inside diameter 22 in FIG. 1). Correspondingly, output 134 represents the lap count (identified as the number of laps 18 in FIG. 1). These output parameters can be determined with relatively high accuracy. Each of these outputs consisting of the outside diameter, inside diameter and lap count are applied as inputs to devices which can calculate the length of the sheet material of the sheet coil 10. This coil length determination is symbolically shown in FIG. 3 as being made by the coil length calculator 136. The output of the coil length calculator 136 is the output shown in FIG. 3 as coil length parameter 140. The coil length parameter 140, in turn, is applied as an input to the previously described average lap gauge calculator 124. With the information consisting of the coil weight 116, material density 118, width 120 and coil length 140, the average lap gauge calculator 124 can readily determine the average lap gauge 126.

As further shown in FIG. 3, the gauge profile apparatus 100 applies the output of the lap gauge calculator 124, consisting of the average lap gauge 126, as an input to what is referred to in FIG. 3 as an average 3D profile calculator 142. Also applied as an input to the profile calculator 142 is the previously described lap profile 114 which comprises the output from the gauge profile system 104. With the lap profile 114 and average lap gauge 126, the 3D profile calculator 142 can generate an estimation of the average 3D profile over the entirety of the length of the sheet coil 10. This is shown as average 3D gauge profile parameter 144. In addition to the output 144 consisting of the average 3D gauge profile, the gauge profile apparatus 100 can also be utilized to generate a parameter shown in FIG. 3 as the peak-to-peak distance 138. These distances can be calculated directly by the coil dimension calculator 128 through the measurement of the parameters of the sheet coil 10.

Figure 4:
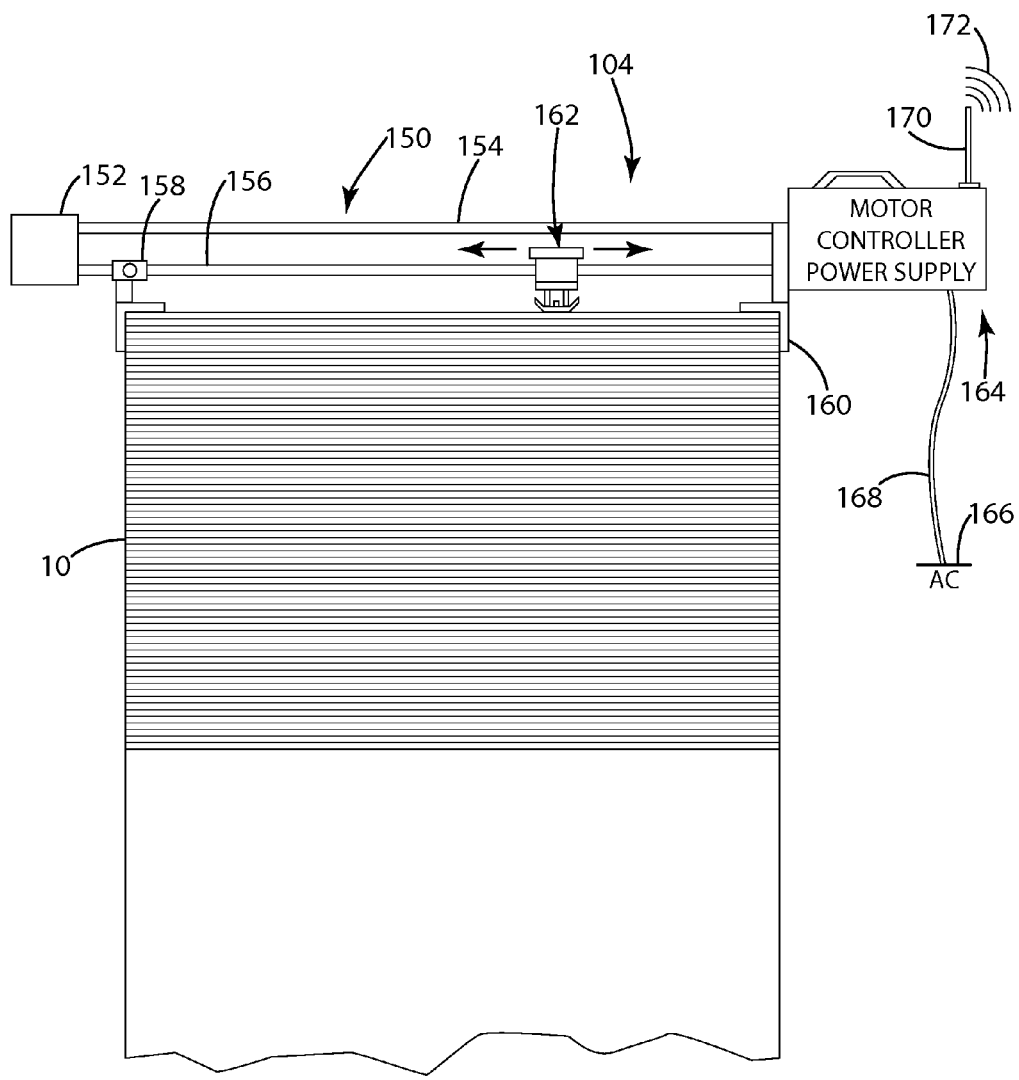
FIG. 4 is a diagrammatic view of a cross section of a coil under test, and the physical positioning of a gauge profile system utilized with the apparatus in accordance with the invention.
Figure 5:
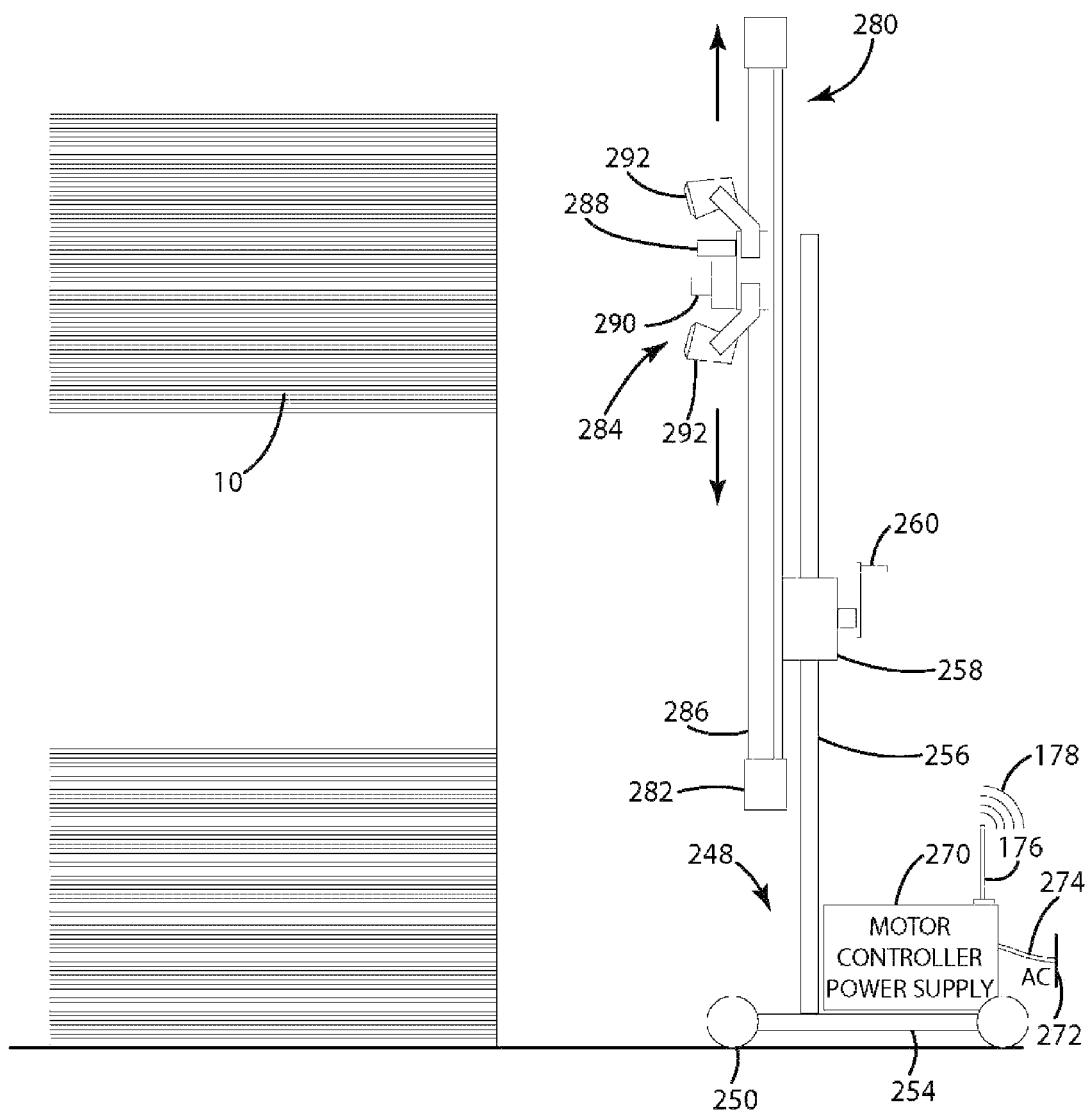
FIG. 5 is a diagrammatic illustration of the relative positioning of the coil under test with a lap count system which may be utilized with the apparatus in accordance with the invention.
Figure 6:
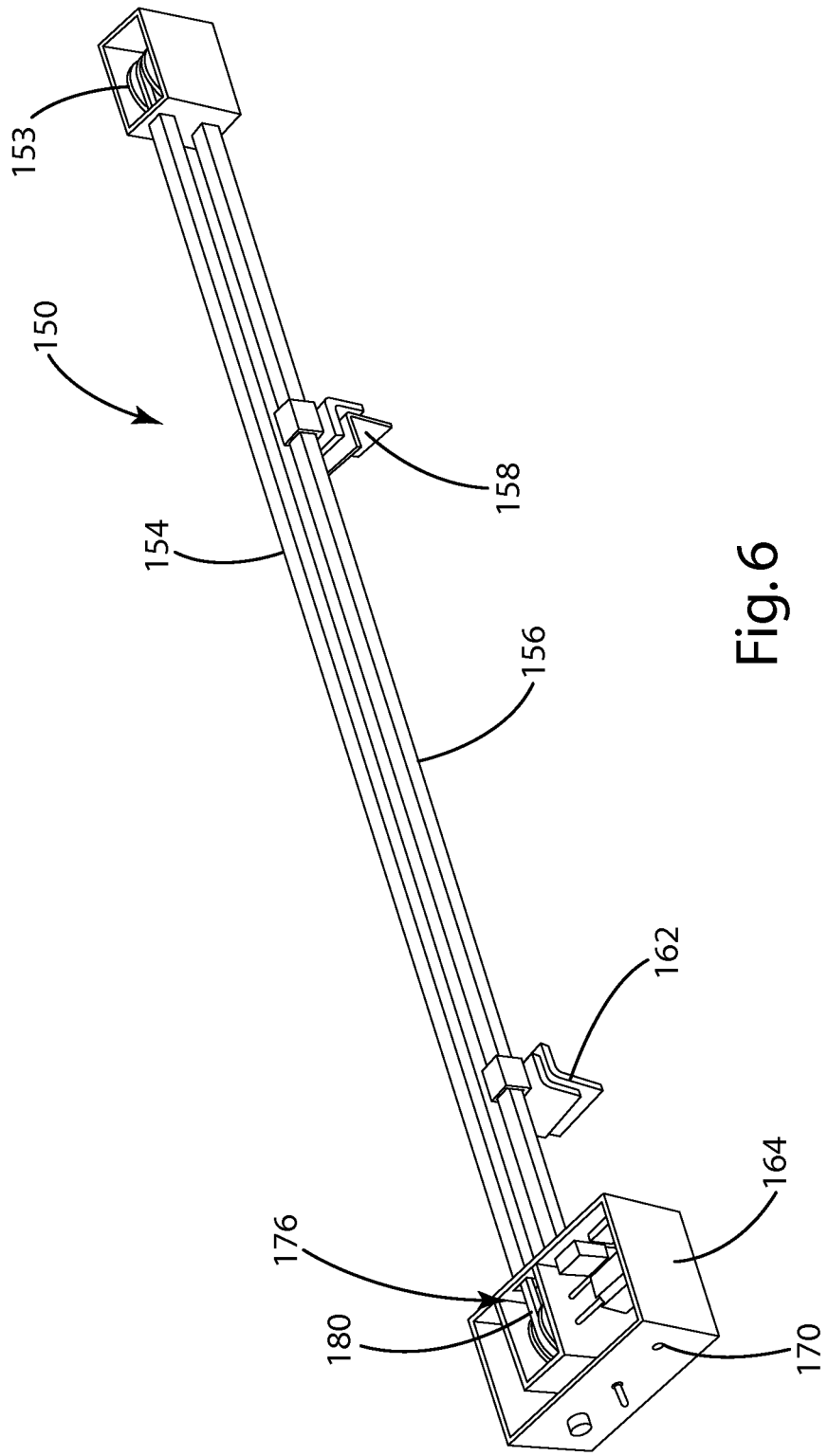
FIG. 6 is a perspective view of a linear slide which may be utilized with the gauge profile system.

Physical element description, as well as additional functional description, will now be provided for the gauge profile system 104, primarily with respect to FIGS. 4 and 7-15. FIG. 4 illustrates relative positioning of the physical configuration of the gauge profile system 104 on the sheet coil 10, with the sheet coil 10 shown in partial cross section in FIG. 4. With reference thereto, the gauge profile system 104 includes a linear slide, the major components of which are also illustrated in FIG. 6. The linear slide 150 includes an end block 152 having a reversal block 153 (see FIG. 6) mounted therein. The linear slide 150 also includes an upper belt arm 154 and a lower belt and slide arm 156, the arms 154 and 156 being spaced apart and parallel to each other. For purposes of securing the gauge profile system 104 to the sheet coil 10 during measurement procedures, the linear slide 150 also includes an end clamp 158 which clamps the linear slide to one end of the sheet coil 10. A second clamp identified as adjacent clamp 160, is utilized to clamp the linear slide 150 to the other edge of the sheet coil 10. In addition to the foregoing, and consisting of one of the principal elements of the gauge profile system 104, a thickness sensor 162 is included which is moveably mounted to the lower belt and slide arm 156. As described earlier herein, the thickness sensor 162 is a commercially available ultrasonic gauge device which will bombard the sheet coil 10 with high frequency sound waves. The timing between wave reflections or echoes can be translated into distance determinations between top and bottom surfaces for the sheet coil 10. The purpose for the linear slide 150 is to provide a means for permitting traverse of the thickness center 162 across the width of the sheet coil 10, while capturing thickness measurements during traversal.

Mounted to the end of the linear slide 150 is a control box 164, which contains both mechanical and electronic elements for the gauge profile system 104. More specifically, the control box 164 can be mounted to the adjacent clamp 160. Power for the control box 164 can be provided as AC power 166 through a power cord 168. Further, if desired, signals can be transmitted between a desktop computer or the like (not shown) and the control box 164 through antenna 170. These signals are illustrated as spatial signals 172 in FIG. 4. It should be noted that FIG. 6 illustrates the linear slide 150 in the absence of the thickness sensor 162.

Figure 13:
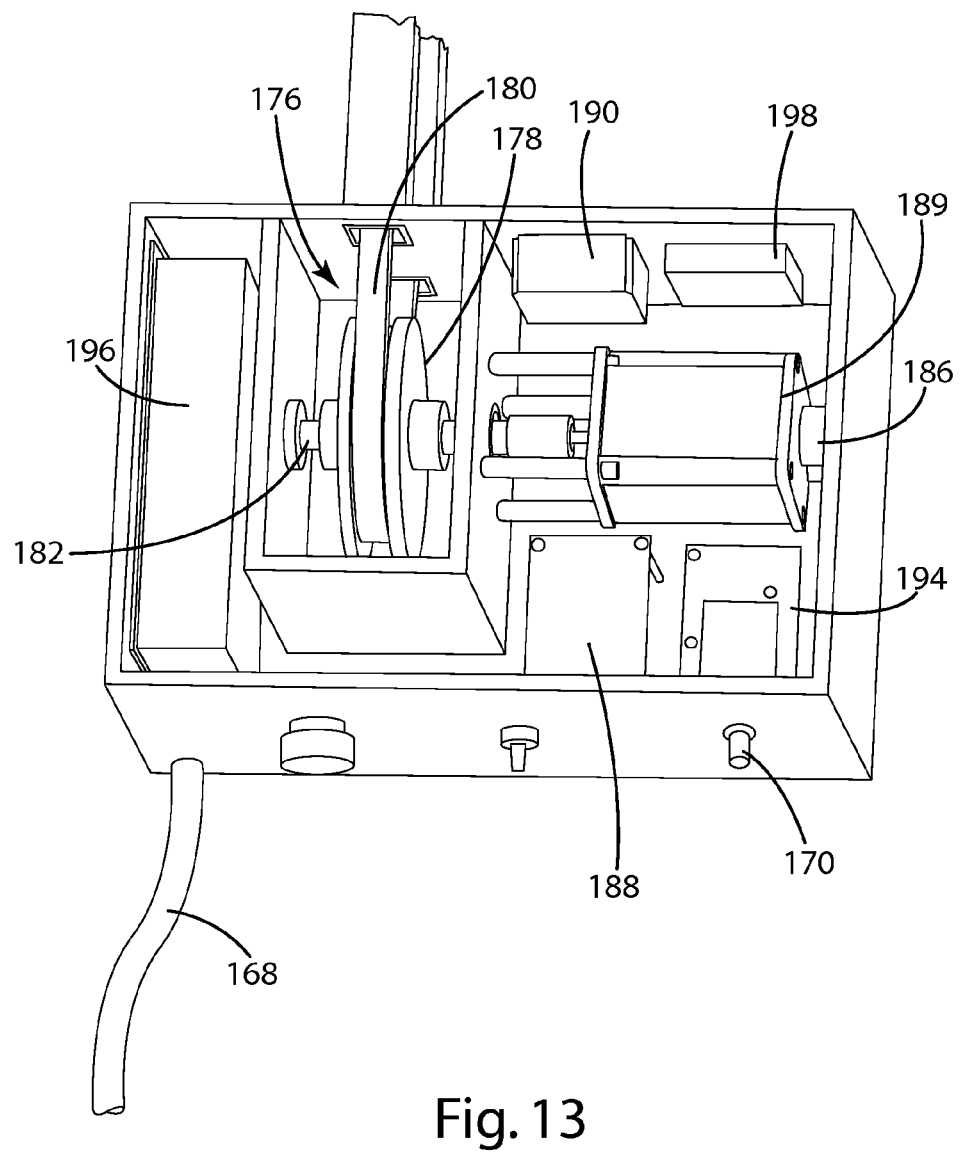
FIG. 13 is a perspective view of the interior of the driven sprocket enclosure and associated components which may be utilized with the gauge profile system in accordance with the invention.
Figure 14:
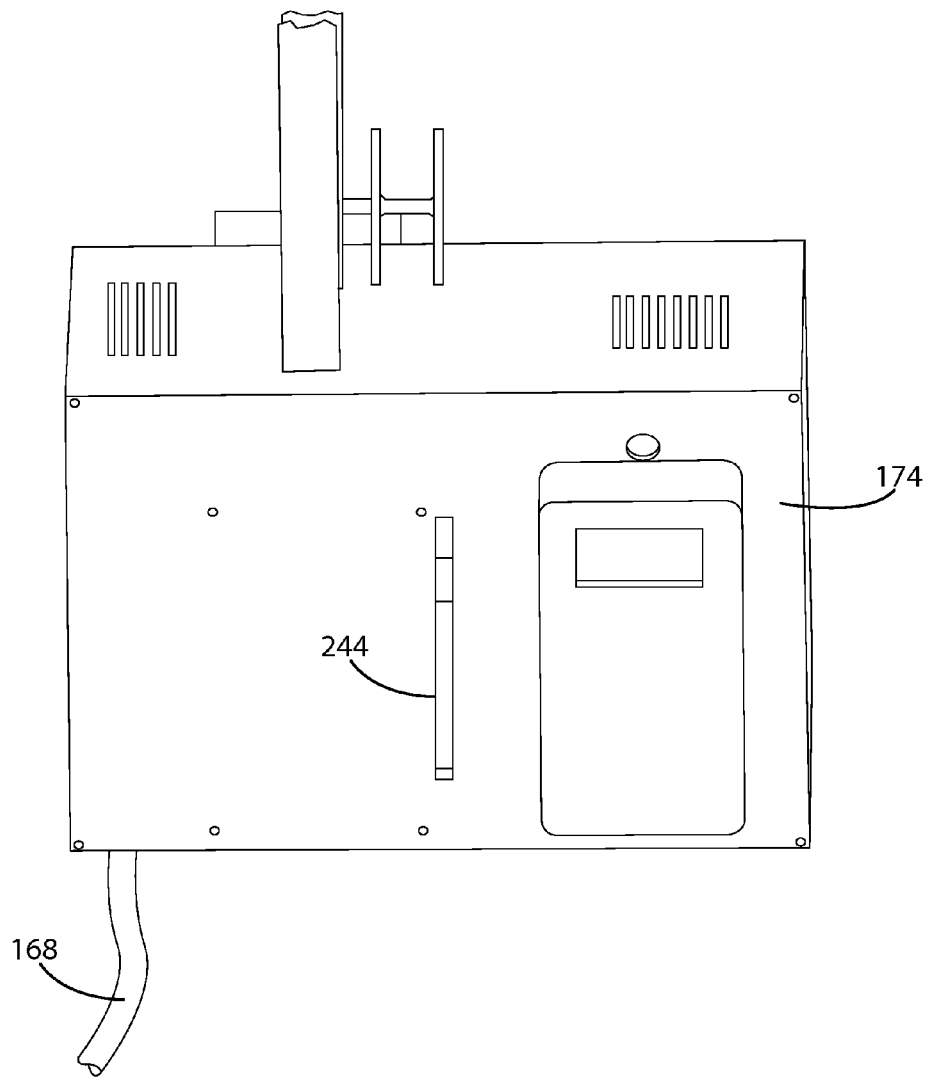
FIG. 14 is a further perspective view of the driven sprocket enclosure illustrated in FIG. 13, but showing the enclosure in a state with the cover secured thereon.

More specifically with respect to FIG. 6, the control box 164 is illustrated with the absence of a control box cover 174, which is illustrated in FIG. 14. As shown primarily with respect to FIGS. 6 and 13, the gauge profile system 104 includes a driver belt system 176, the major components of which are located within the control box 164. As shown primarily in FIG. 13, the driver belt system 176 includes a drive pulley 178 having a stepper motor belt 180 positioned on the pulley 178. The pulley 178 is attached to a drive axle 182.

Figure 7:
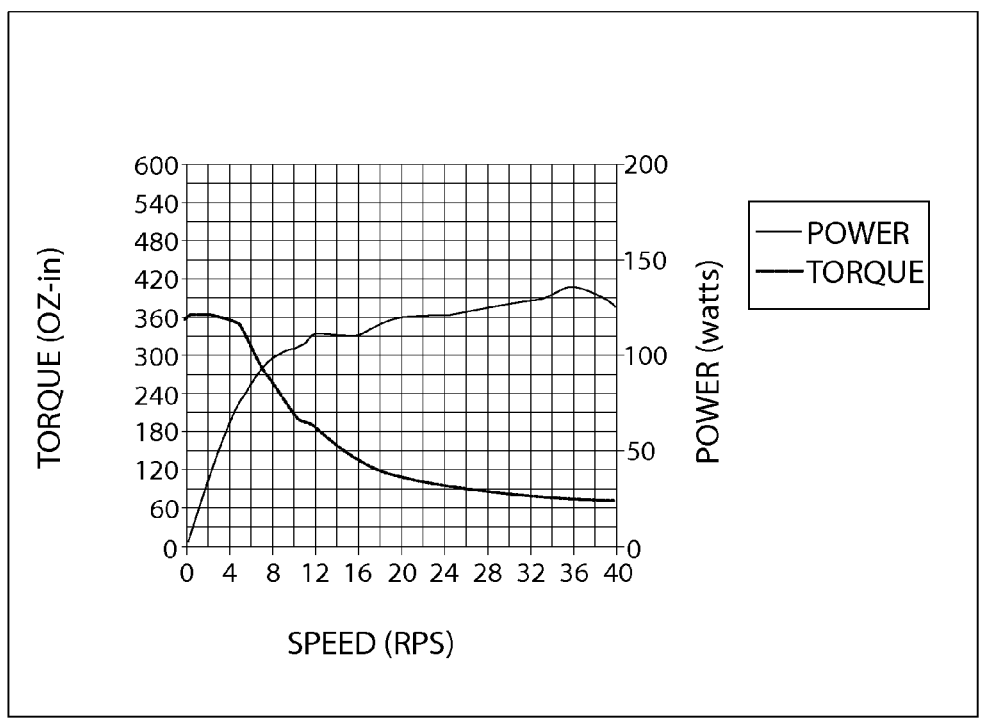
FIG. 7 is a graphic illustration of the relationship among power, speed and torque characteristics of a stepper motor which may be utilized with the gauge profile system in accordance with the invention.
Figure 15:
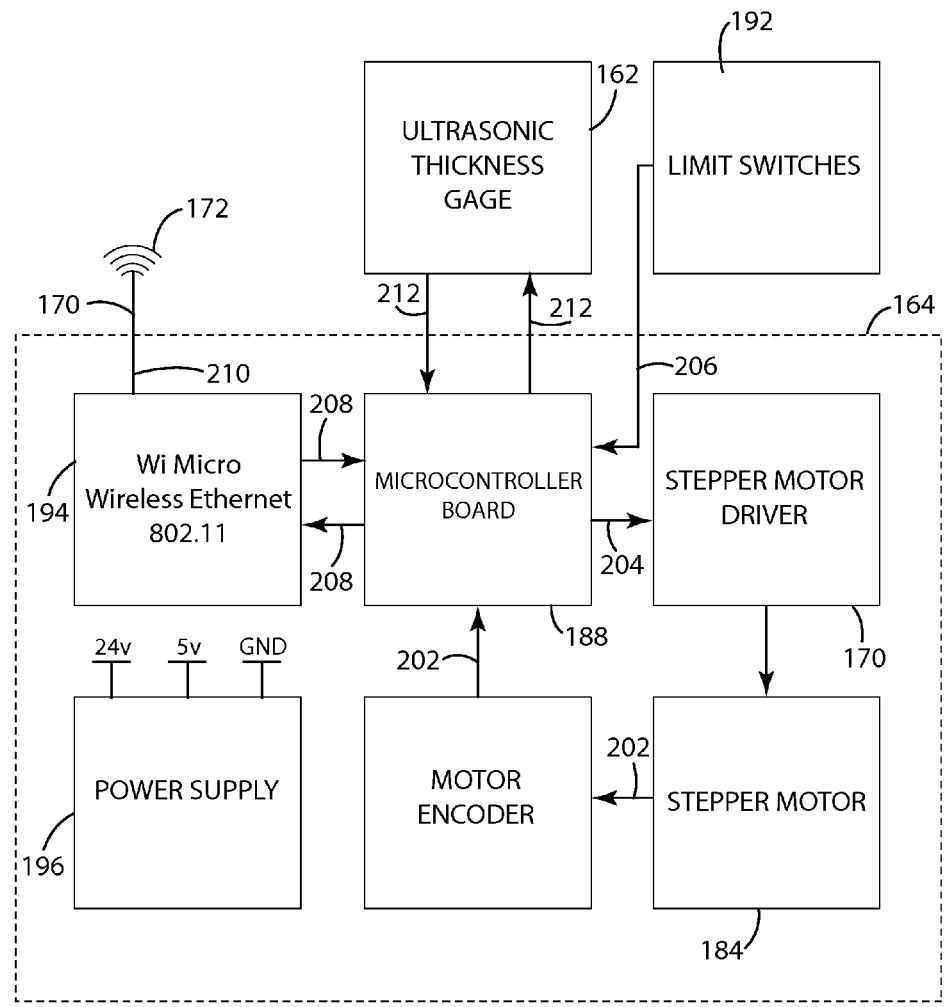
FIG. 15 is a block diagram of certain components associated with the control system for the gauge profile system in accordance with the invention.

With reference now to FIGS. 4,6,13 and 15, the internal components of the control box 164 include a stepper motor 184. The stepper motor 184 can be a commercially available product. For example, a stepper motor which the inventors have found to be operable in testing of an exemplary gauge profile system 104 is one which is utilized for low speed and low torque applications. The motor also should have relatively high accuracy and high resolution characteristics. In this regard, a torque, speed and power graph for a stepper motor 184 which may be utilized in accordance with the invention is illustrated in FIG. 7. With further reference primarily to FIGS. 13 and 15, the gauge profile system 104, within the control box 164, also includes an encoder 186. The encoder receives signals on symbolic line 200 from the stepper motor 184. These signals are digitally encoded and applied on symbolic line 202 as input to a microcontroller 188. The encoder signals applied as digital input signals to the microcontroller 188 on line 202 provide various motor characteristic information, including position information for the microcontroller 188. In a feedback configuration, the microcontroller 188 also applies digital signals on line 204 as input signals to the stepper motor driver 190. The physical representation of the stepper motor driver 190 is illustrated in FIG. 13, and the symbolic functional representation is illustrated in FIG. 15. The digital signals applied from microcontroller 188 on line 204 to the driver 190 essentially comprise control signals for the driver 190 to appropriately operate the stepper motor 184 so as to cause the thickness sensor 162 to traverse the sheet coil 10.

In addition to the foregoing elements, the gauge profile system 104 also includes limit switches 192 which are located outside of the control box 162 and are positioned adjacent the clamps 158 and 160. The limit switches 192 operate so as to limit traversal of the thickness sensor 162 along the lower belt and slide arm 156. The limit switches 192 are conventional in nature and commercially available. The limit switches 192, when actuated by certain positions of the thickness sensor 162, operate so as to apply digital input signals to the microcontroller 188 on symbolic line 206. In turn, the microcontroller 188 will be responsive to the digital signals from the limit switches 192 on line 206 to generate appropriate digital signals on symbolic line 204 to the stepper motor driver 190, so as to control the movement of the stepper motor 184.

In addition to the foregoing elements, the gauge profile system 104, within the control box 164, also includes a wireless board 194. Serial digital signals can be applied in a bidirectional manner between the microcontroller 188 and the wireless board 194 on symbolic lines 208. For example, the wireless board 194 may include a WiMicro Wireless Ethernet configuration with designation number 802.11. The wireless board 194 can transmit and receive signals on line 210, which is attached to the antenna 170 for purposes of transmission/reception of spatial signals to a remotely located computer (not shown).

As further shown in FIG. 15, the microcontroller 188 is appropriately connected to the ultrasonic thickness sensor 162 for purposes of applying and receiving signals on symbolic lines 212. These signals may be transmitted on lines 212 through RS232 communication interfaces. In this manner, control signals can be applied from the microcontroller 188 to the thickness sensor 162, while correspondingly, signals indicative of thickness can be generated by the thickness sensor 162 and applied as input signals to the microcontroller 188.

As shown primarily in FIGS. 8, 9 and 10, the ultrasonic thickness sensor 162 is mounted to a linear bearing 216, specifically illustrated in FIG. 8. The linear bearing 216 is a conventional bearing having a channel 218 longitudinally extending therethrough. A set of bearing plugs 220 are located on each of the four opposing top, bottom and side surfaces of the linear bearing 216. The bearing 216 is utilized to appropriately move the thickness sensor 162 along the lower belt and side arm 156. As shown in FIGS. 9 and 10, each of the bearing plugs 220 is configured so as to be threadably received within the surfaces of the linear bearing 216. The actual bearing plug surfaces 222 provide bearing surfaces against which the lower belt and slide arm 156 will abut during movement of the thickness sensor 162. The linear bearing 216 and bearing plugs 220 are commercially available and may be obtained, for example, from Frelon.

Figure 11:
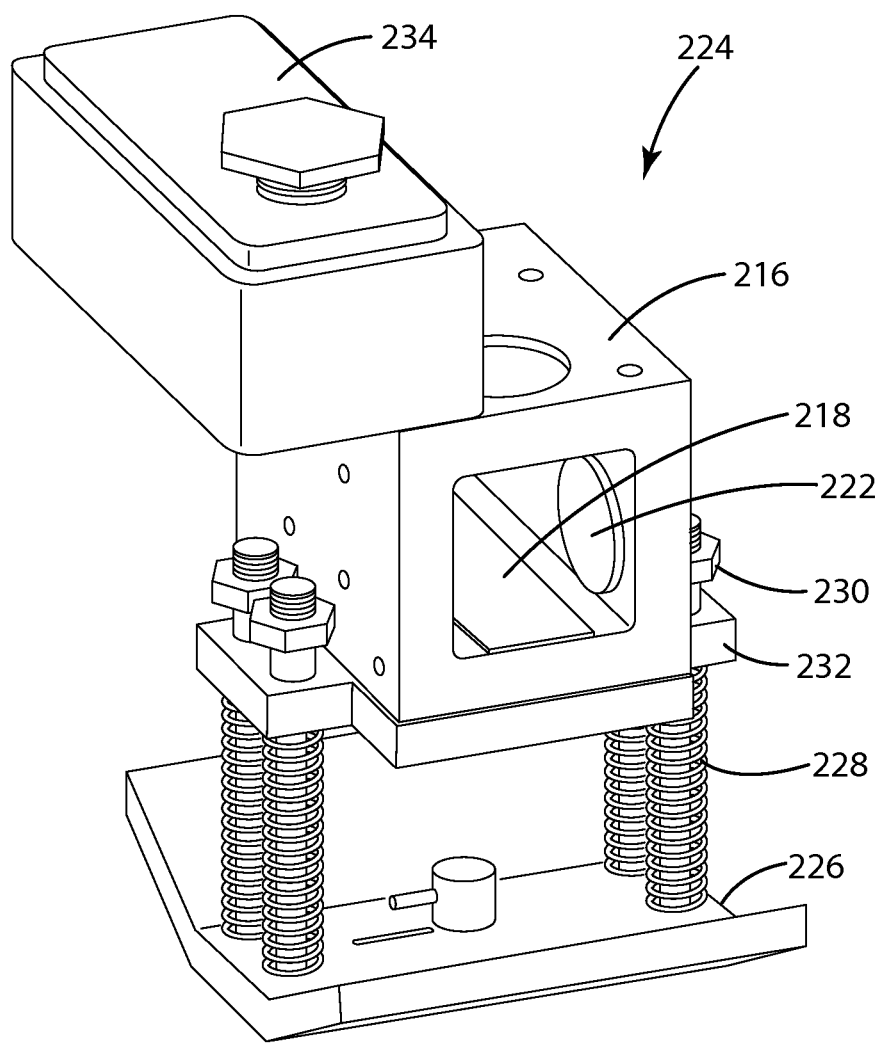
FIG. 11 is a perspective view of a platform and clamping configuration for the sensor utilized with the gauge profile system in accordance with the invention.

During operation, the thickness sensor 162 is mounted onto a sensor sled 224, primarily shown in perspective view in FIG. 11. With reference thereto, the sensor sled 224 includes the previously described linear bearing 216 having bearing plugs 220 with bearing plug surfaces 222. Further, the linear bearing 216 includes the channel 218 through which is received the lower belt and slide arm 156. The sensor sled 224 also includes a lower sled plate 226, onto which the sensor 162 may be appropriately mounted. The sled plate 226 is secured below the linear bearing 216 through the use of bolts 228, nuts 230 and a support plate 232 on which is mounted the linear bearing 216. A clamp 234 is utilized to adjustably secure the linear bearing 216 onto the lower belt and slide arm 156, with the adjustability being with respect to the "tightness" between the arm 156 and the bearing plugs 220.

Figure 12:
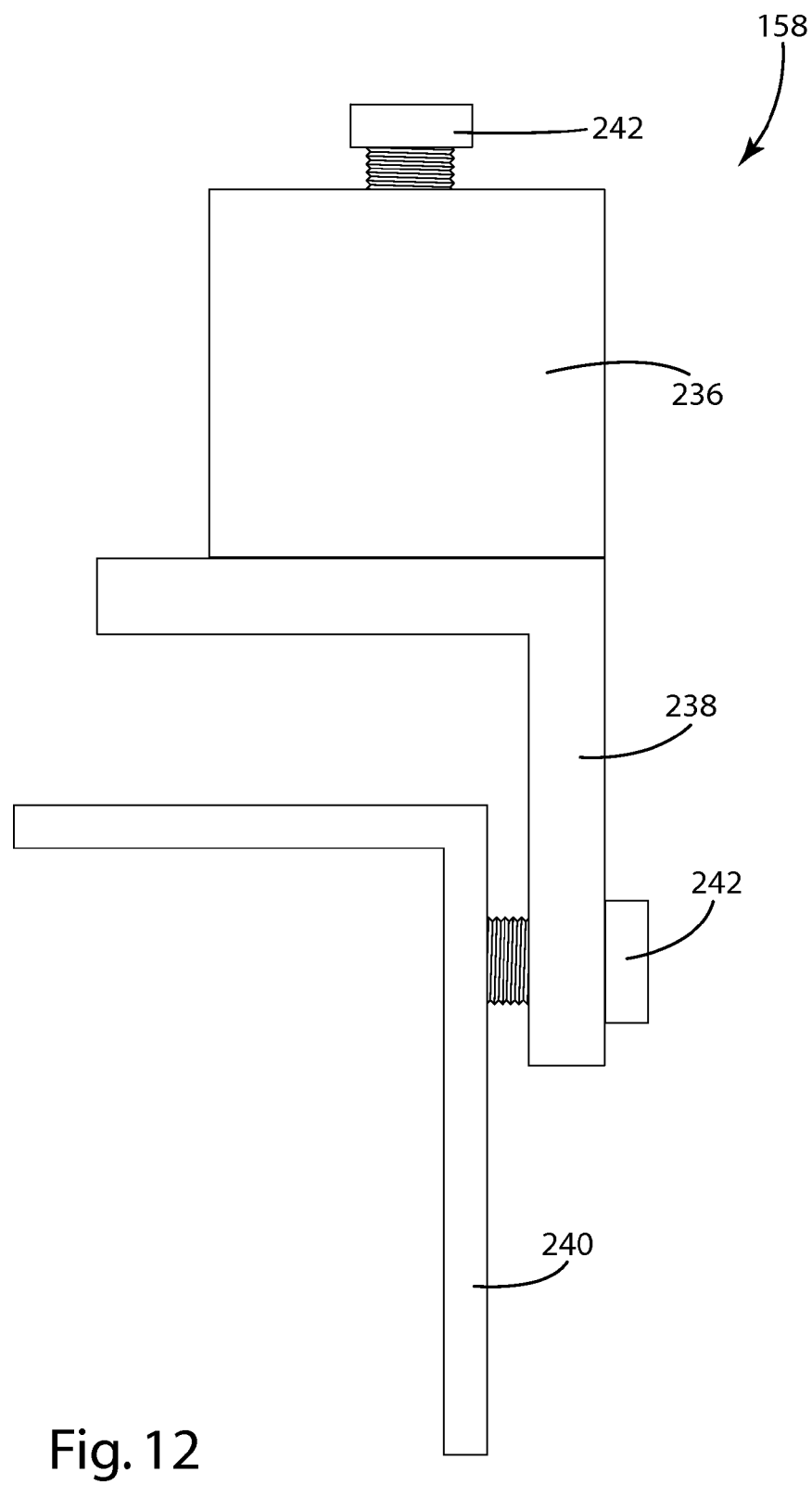
FIG. 12 is a partially elevation and partially diagrammatic view of certain components of the sensor platform and clamping configuration illustrated in FIG. 11.

FIG. 12 illustrates components of the end clamp 158. With reference thereto, the end clamp 158 includes a stopper sleeve 236, preferably having a rubber backing on the sleeve 236. Integral with or otherwise connected to the stopper sleeve 236 is a sleeve bracket 238 positioned below the stopper sleeve 236. The sleeve bracket 238 has a right-angle configuration as illustrated in FIG. 12. The clamp 158 also includes an L-shaped bracket 240, also preferably having a rubber backing. The stopper sleeve 236 is equipped with a stopper set screw 242 at the upper portion thereof. A second stopper set screw 242 is also positioned at the lower end of the sleeve bracket 238, and is utilized to adjust the relative positions of the sleeve bracket 238 and the L-shaped bracket 240. The upper set screw 242 can essentially provide for coarse adjustment, while the lower stopper set screw 242 provides for fine adjustment.

A convenient way for transporting the components of the gauge profile system 104 is illustrated in FIG. 14. As shown therein, the control box 164 can be enclosed with the cover 174. If desired, the thickness sensor 162 can be secured to the control box cover 174 through the use of backing, such as Velcro. Also, a lift handle 244 can be provided.

The lap count system 106 will now be described in greater detail, primarily with respect to FIGS. 5 and 16-18. With respect first to FIGS. 5, 16 and 17, the lap count system 106 includes a lap count system support stand 246. The lap count system support stand 246 includes a lower support 248 consisting of several components. More specifically, the lower support 248 includes a series of four casters 250. Each of the casters 250 is rotatably secured to a leg support 254 through a clevis 252, which permits the corresponding caster 250 to rotate relative to the clevis 252. Connected to or otherwise integral with the leg support 254 at the center point thereof is a vertical leg 256 extending upwardly therefrom. Positioned as desired along the vertical leg 256 is a crank box 258. The crank box 258 can be operated and is conventionally structured so as to move along the vertical leg 256 through a conventional rack and pinion configuration comprising a conventional pinion gear 266 and rack 267 which is vertically mounted along one side of the vertical leg 256. The crank box 258 includes a set of three sides 262. Extending through one of the sides 262 is a conventional crank 260 which, in turn, is connected to the pinion gear 266 through a conventional axle. Mounted to a fourth side of the crank box 258 is a linear slide mounting 264. The linear slide mounting 264 is connected through pins 268 to the crank box 258 and to a linear slide 280. As shown primarily in FIG. 5, the lap count system 104 also includes a control box 270 which can be positioned in any suitable manner on the lower support 248. The internal components of the control box 270 will be described in subsequent paragraphs herein. As further shown in FIG. 5, power is supplied to the control box 270 as AC power 272 running through power cord 274. For purposes of wireless communication to a desktop computer or the like, the control box 270 also includes an antenna 276 connected to appropriate components within the control box 270 for transmitting and receiving spatial signals 278 from the computer.

The linear slide 280 is extremely similar in structure and configuration to the previously described linear slide associated with the gauge profile system 104. More specifically, the linear slide 280 includes a stepper motor 282 which can be utilized for purposes of moving a set of sensing equipment 284 along slide arm 286. The sensing equipment 284, as previously described herein, includes a distance sensor 288 and camera 290. For purposes of insuring adequate illumination, a set of lights 292 is also included with the sensing equipment 284. With the foregoing configuration, the sensing equipment 284 can be moved vertically along the slide arm 286 in accordance with the functional operation of the motor 282.

FIG. 18 is a functional and partially diagrammatic illustration of the various components of the lap count system 106. With reference thereto, the control box 270 is shown as including a micro-controller 294 which can be similar to the micro-controller previously described with respect to the gauge profile system 104. Bidirectional lines 296, comprising what may be RS232 and RS485 interfaces can be utilized to transmit digital power signals to a servo amplifier 298, and to transmit and receive bidirectional signals in the form of control signals. The servo amplifier 298 is utilized to control the motor and encoder 282. The motor 282 is controlled through the servo amplifier 298, and encoding signals can be transmitted bidirectionally on lines 300 between the encoder 282 and the servo amplifier 298.

As previously described, the lap count system 106 includes the ultrasonic distance sensor 288. The distance sensor 288 is controlled by the micro-controller 294 through analog signals transmitted as input signals to the sensor 288 on lines 302. Lines 302 are bidirectional in that signals can also be transmitted back to micro-controller 294, indicative of the distance sensed by the sensor 288.

In addition to the foregoing, and as also previously described, the lap count system 106 includes a DVT area scan camera 290. The scan camera 290 is also under control of the micro-controller 294 through signals transmitted as digital power signals on line 304. Lines 304 are bidirectional and image signals can be transmitted back to the micro-controller 294 on lines 304.

The lap count system 106 can also include a wireless router 306 which is commercially available and conventional in nature. The wireless router can transmit and receive signals on an Ethernet basis to and from the micro-controller 294. In addition, signals can be transmitted from the router 306 and received by the router 306 to and from the antenna 276. These signals would initially be in the form of spatial signals 278 transmitted to or received from a remote computer (not shown). In addition to the foregoing, signals can also be transmitted to and from the router 306 on lines 310 with respect to the camera 290. Finally, the control box 270 includes a power supply 312. With this configuration, and with the functional operation of the lap count system 106 as previously described herein, the average thickness of a coil can be computed by counting the exact number of laps of the coil, as well as the inside and outside diameters of the coil. With this information combined with a width measurement, the volume of the coil can be determined. With the volume combined with a weight measurement, the average gauge of the coil can also be determined. In accordance with all of the foregoing, and as shown in the drawings, a three-dimensional gauge projection can be provided through the use of the gauge profile system 104 and the lap count system 106.

If desired, and in accordance with certain concepts of the invention, it is possible to utilize a processing algorithm with respect to the images sensed by the camera 290. This is directed in substantial part to detect the number of laps with as much accuracy as possible. For purposes of detecting the laps, the algorithm will look at the changes in light intensity across the width of the image produced by the camera 290. Because of the vertical symmetry in the image, such information can be taken from a relatively small horizontal window. This fact allows an algorithm to take advantage of the camera's partial image acquisition. That is, using partial image acquisition, the camera 290 can capture and process a small portion of the image. This reduces the amount of data that must be stored in memory and processed, which decreases the time required to process each image.

Figure 19:
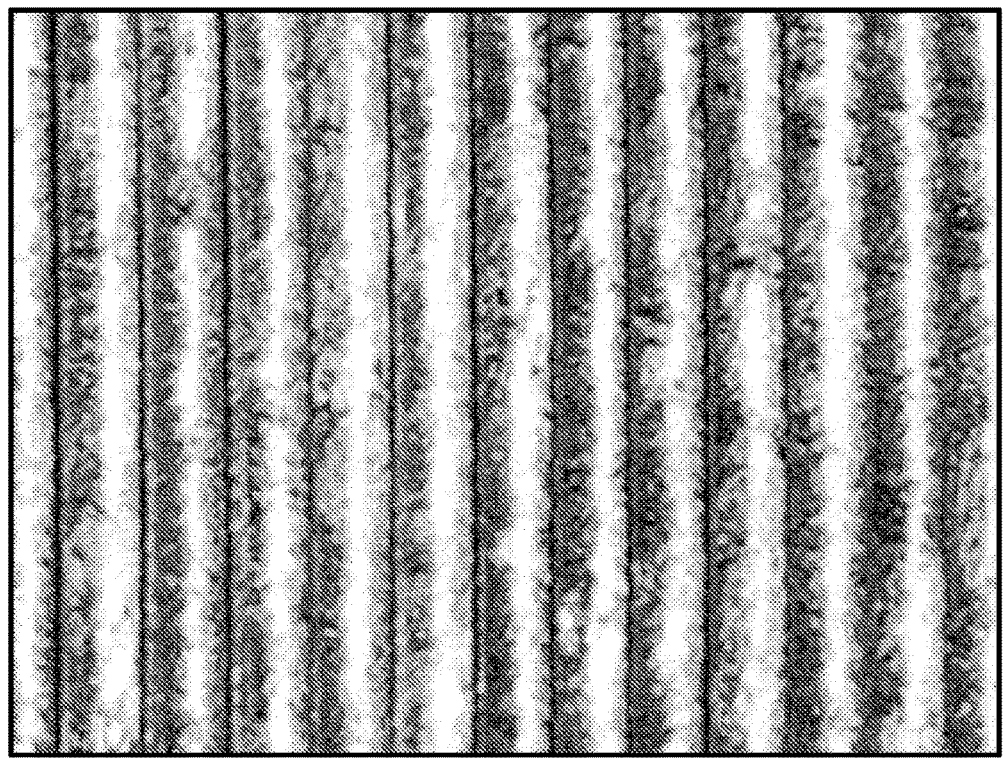
FIG. 19 is an image in an original state which was produced from a prototype of the lap count system in accordance with the invention.
Figure 20:
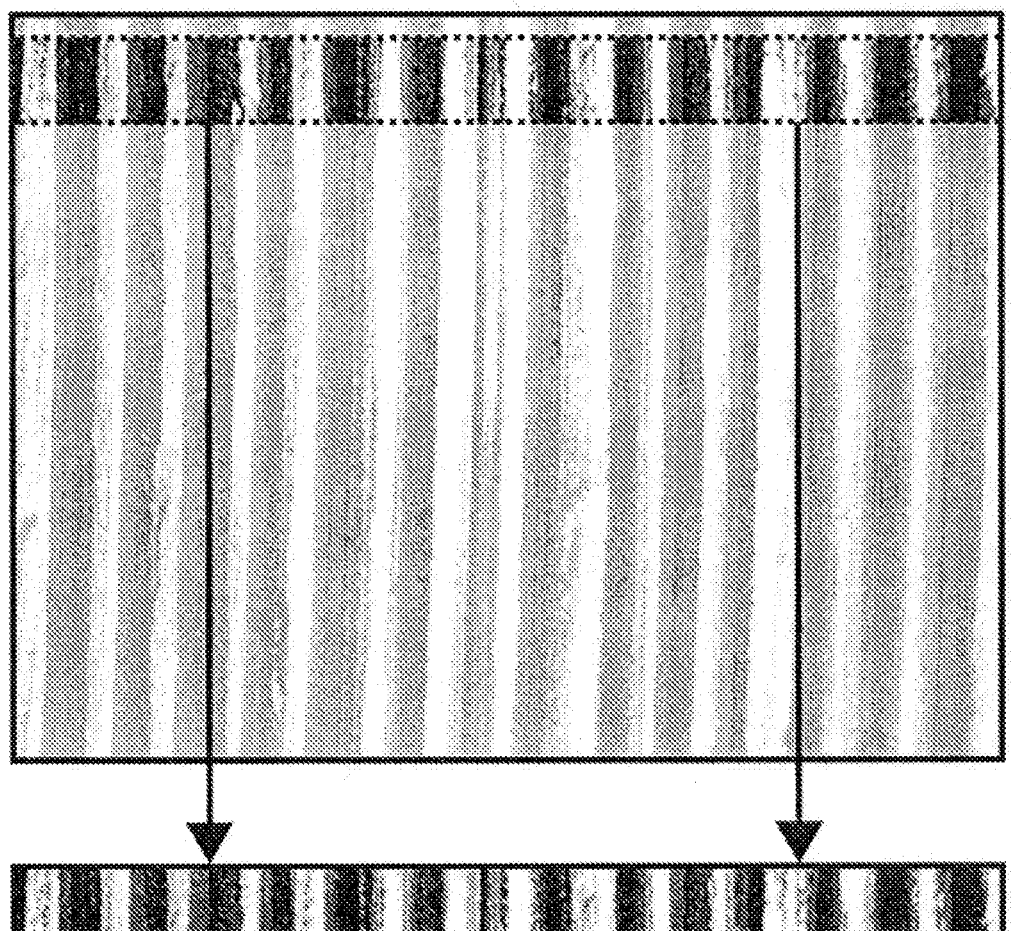
FIG. 20 is an illustration of a partial image acquisition utilizing processes performed by the lap count system in accordance with the invention.
Figure 21:
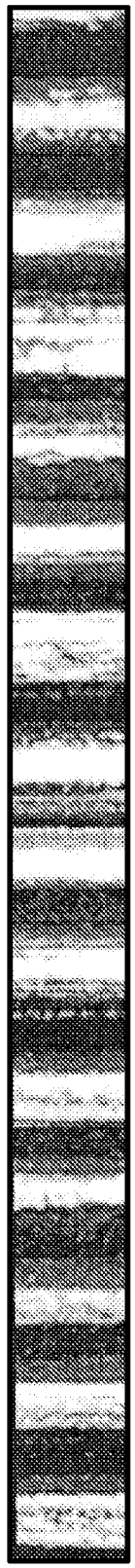
FIG. 21, like FIG. 19, illustrates an original image of the coil laps as produced by the lap count system in accordance with the invention.
Figure 22:
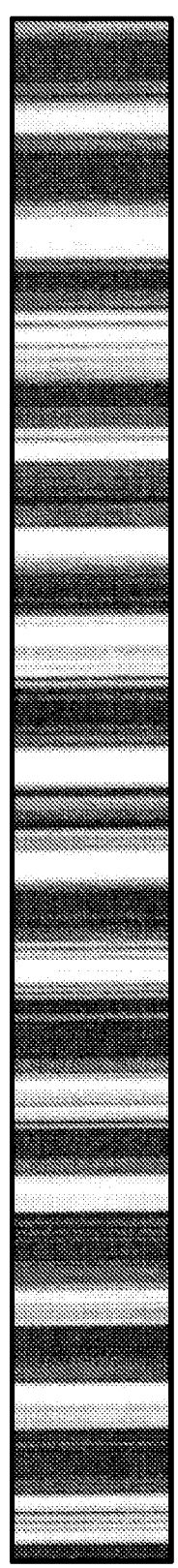
FIG. 22 is an image of the laps illustrated in FIG. 21 following an image averaging procedure undertaken by the lap count system in accordance with the invention.

FIG. 19 illustrates an original image of the lap count as produced by the camera 290. Correspondingly, FIG. 20 illustrates the partial image acquisition process. Once the partial image has been captured, it can be averaged along the columns (the columns representing the laps) to produce a single roll of pixels representative of the changes in light intensity across the image. An example of such averaging is illustrated in FIG. 22, which shows the result of the vertically averaged image from the original image illustrated in FIG. 21.

Figure 23:
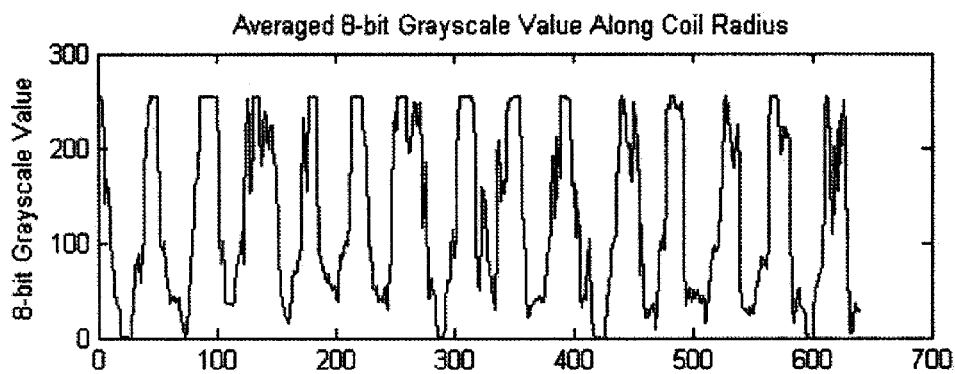
FIG. 23 illustrates a plot of grayscale values obtained by the lap count system in accordance with the invention, along the coil radius.

In this regard, each pixel is represented by an 8-bit grayscale value, where zero represents black and 255 represents white. FIG. 23 illustrates a plot of the grayscale values along the length of the averaged image. Each lap is visible as a peak in the graph. The low areas in the graph are caused by the dark regions between the laps, and the high areas are caused by the bright edges of the laps.

Figure 24:
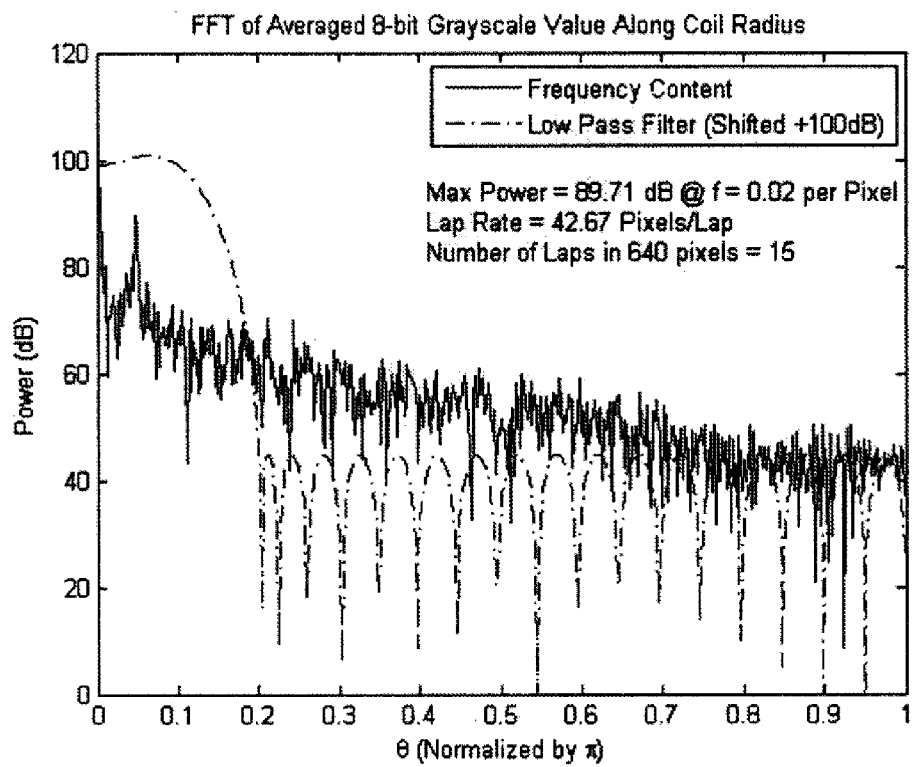
FIG. 24 is an illustration of the frequency characteristics of a low pass filter which may be utilized with the lap count system, for purposes of noise reduction.
Figure 27:
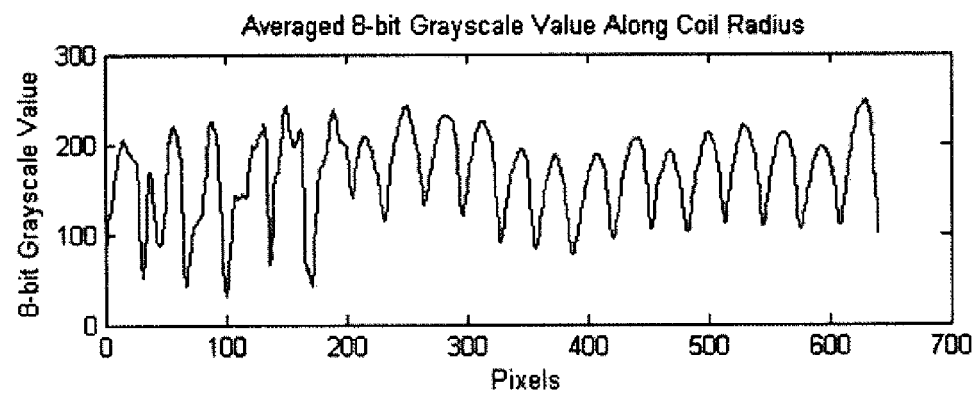
FIG. 27 is a plot of the average grayscale values along the coil radius generated through the use of a lap count system.
Figure 28:
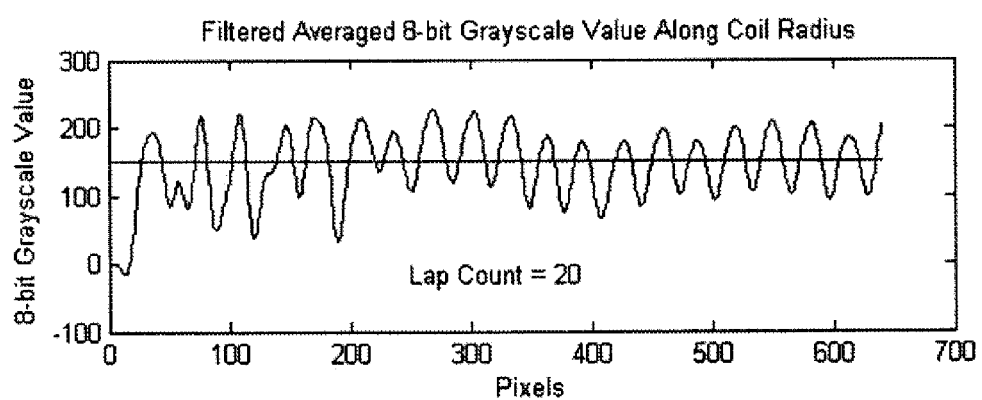
FIG. 28 is similar to FIG. 27, but illustrates the plot of grayscale values after focusing techniques have been applied to the lap count system in accordance with the invention.

The peaks, however, would be difficult to detect because of the noise caused by imperfections in the surface of the sheet coil 10 and non-ideal lighting. In order to reduce the noise in the signal, a low pass filter, conventional in nature, may be applied to the data. The frequency component of the signal, along with the low pass filter result, is shown in FIG. 24.

The filtered data is illustrated in FIG. 25. As shown therein, the noise in the signal has been greatly reduced, and the peaks can be easily counted with a set threshold. Also, the location of each peak can be found relative to the edge of the frame. It is important to note that the filter may introduce a phase shift. However, because a finite impulse response filter is used, the phase shift will be linear. Accordingly, the filter will only create a delay in the signal, for which compensation can be easily applied.

The camera can then transmit the peak locations within the image to the computer. In a physically realized experiment, the in-dash camera processing algorithm was implemented on the Cognex 535 area scan camera using the DVT Intellect software. The operation of the algorithm was verified, in addition to the camera's communications. Also, a preprocessing step was added, which increased the contrast of the image. The camera was capable of executing the entire algorithm from image acquisition to data output at a rate greater than 40 Hz. This exceeds the desired 30 Hz.

With respect to post-camera processing, as the camera moves along the side of the coil 10, it will transmit the peak location to the computer. The computer will track the peaks as they move through the field of view. As the peaks exit the frame, the computer will increment a count. After traversing the entire side of the coil, this count will be equal to the total number of laps in the coil.

It has been found that in order for the computer to track the laps, the camera must capture frames at a rate of at least twice the rate at which the laps move through the frame. Because the frame rate is fixed, the vertical velocity should be adjusted, depending upon the gauge of the coil to guarantee that enough samples are taken to properly represent the laps.

In addition to the camera algorithm, focus testing can also be implemented. That is, any changes in the distance between the coil sidewall and the camera may affect the focus of the captured image. Depending upon the lens, lighting and shutter speed, the camera will be able to focus at a set distance away, within a set focal range. However, if the coil sidewall moves out of range during a test, captured images may become blurry. To determine focus capability, a damaged coil was photographed over the damaged region. The resulting image is illustrated in FIG. 26. As shown therein, the left-most portion of the image is in focus. However, the right side of the image is out of focus because the damaged laps have been pushed toward the camera. An algorithm was then applied, with the results shown in FIGS. 27 and 28. Specifically, it was shown that the algorithm was able to successfully count the laps, even though certain of the laps were out of focus. In the unfiltered averaged data, the left-hand side of the image that was in focus had a relatively greater high frequency content. The right-hand side that was out of focus had much less high frequency content, and was smoother. However, even with the loss of this data, the algorithm can easily identify out-of-focus laps.

As earlier stated, the gauge profile apparatus in accordance with the invention can use a gauge profile system distinguishable from the gauge profile system 104. A second embodiment of a gauge profile system in accordance with the invention is described herein as gauge profile system 400 and is illustrated in FIGS. 29-60. Again, it should be emphasized that the resultant functions and purposes of a gauge profile apparatus utilizing the gauge profile system 400 is the same as a gauge profile apparatus using the gauge profile system 104.

From the prior description, it is apparent that although the gauge profile system 104 provides significant advantages over the prior art, the gauge profile system 104 is somewhat complex and is difficult to be handled by only one person. Unfortunately, steel companies will often only have one person taking care of receiving of steel coils. Further, as occurs with any mechanical invention, the greater the number of moving parts, the higher the probability of maintenance and repair necessities. Also, the track system utilized with the gauge profile system 104, as a result of its elongated configuration, may be damaged within the types of environments which exist in steel warehouses.

As described in subsequent paragraphs herein, the embodiment of the gauge profile system 400 provides a production-ready and hand-held measuring device capable of measuring variations of the thickness of the top layer of a steel coil from one edge to the opposite edge, as well as the position from the leading edge of the coil that each measurement is taken. The gauge profile system 400 provides for a relatively high precision in terms of measuring thickness, while also providing a relatively wide range. In addition, linear position measurements are also provided with a relatively high precision, and with a relatively wide range. Of particular significance, the gauge profile system 400 as used for measuring the sheet coil 10 is preferably handled and relatively easy to operate by one person. Also, the measuring process should preferably take less time than known methods of measurement in the prior art. Also, it is advantageous if the gauge profile apparatus is able to store or upload measurements for further analysis. Still further, and again with respect to the types of environments which exist in steel warehouses, it is preferable for the device to be able to operate in a relatively severe environment, including temperatures which may reach 100 degrees Fahrenheit. In addition, it is advantageous if the gauge profile system being used is capable of interfacing with a computer or network so as to download daily receiving schedules, as well as upload measurement data.

Figure 29:
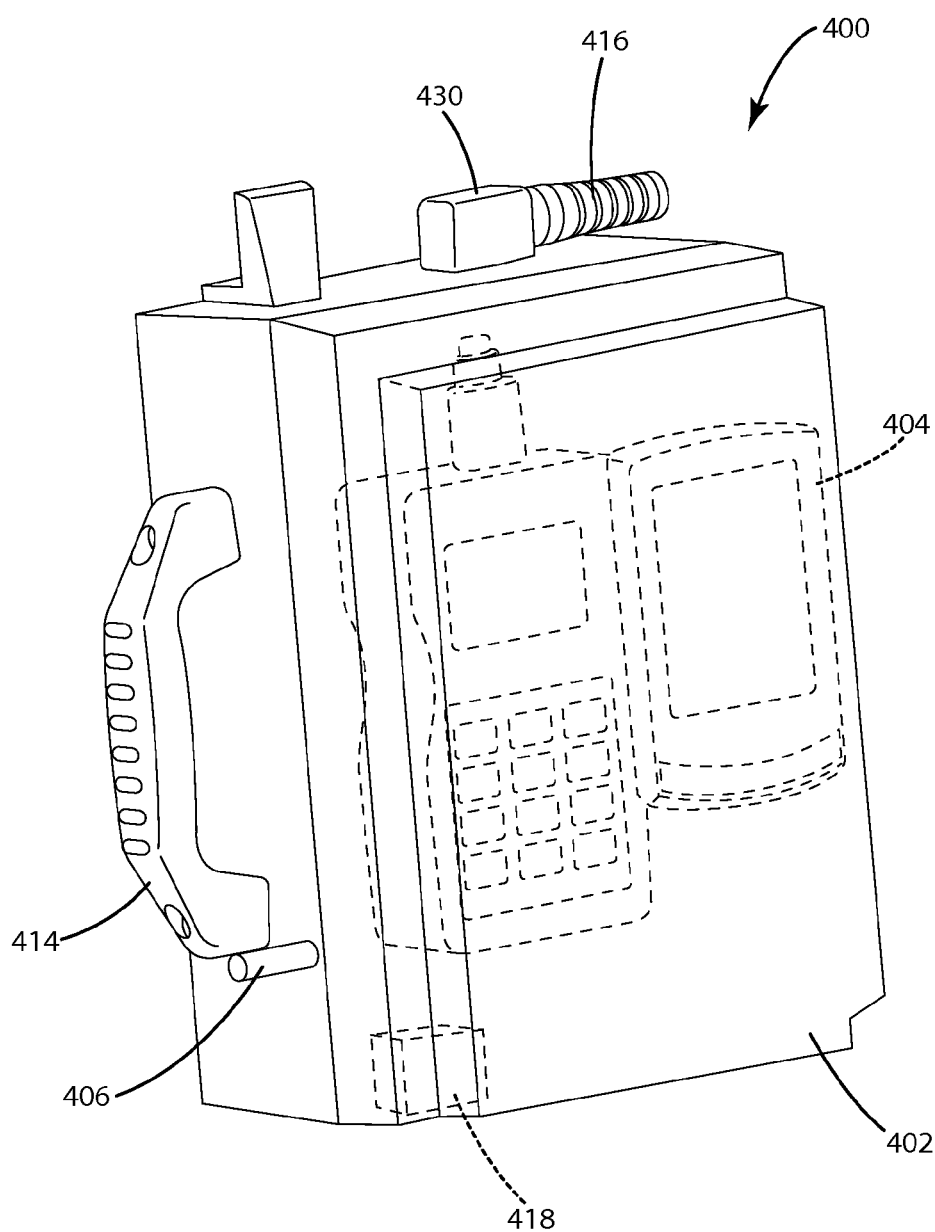
FIG. 29 is a perspective view of a second embodiment of a gauge profile system which may be utilized in accordance with the invention.
Figure 30:
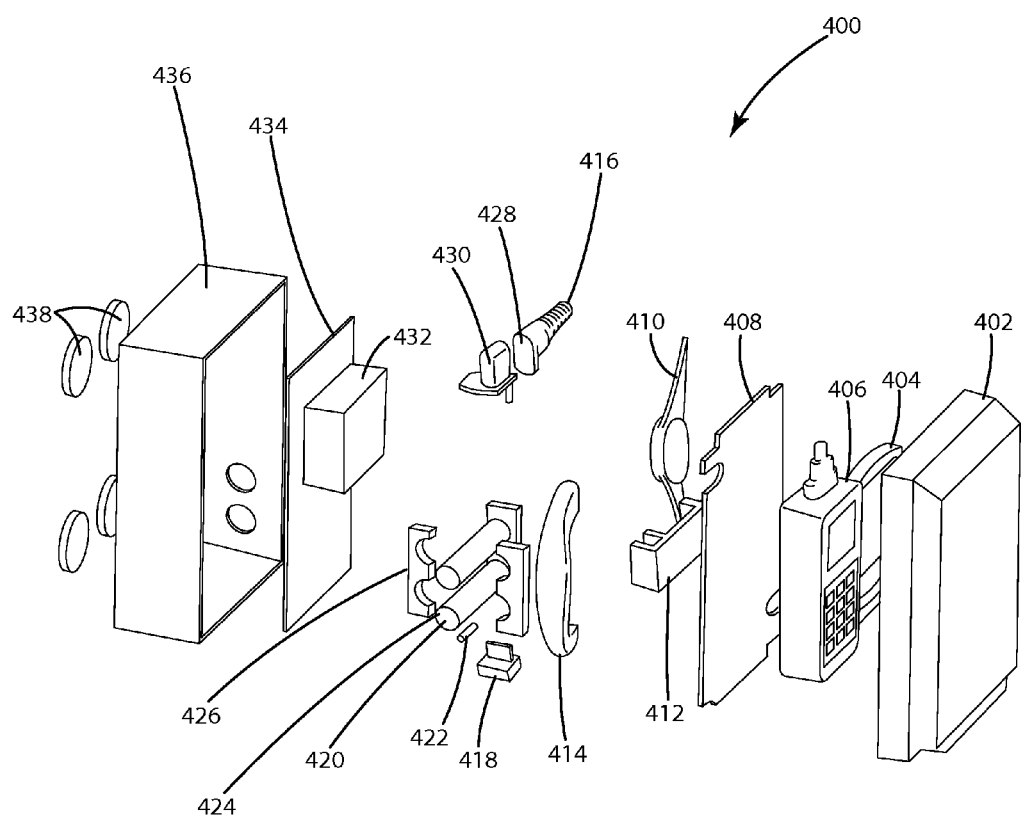
FIG. 30 is an exploded view of the gauge profile system illustrated in FIG. 29.

These and other advantages are provided by the gauge profile system 400 illustrated in FIGS. 29-60. A perspective view of the entirety of the profile system 400 is illustrated in FIG. 29. An exploded view of the case assembly for the profile system 400 is illustrated in FIG. 30 and individual component parts are illustrated in FIGS. 31-44. The physically realized prototype has a weight of approximately 6.4 lbs. Power is provided by a PDA battery, while an embedded device of the system is powered from 4 rechargeable AA batteries. The system is capable of at least 30 minutes of continuous use, and employs an access door for fast battery charges.

Measurement thickness tolerances are in the range of 0.0001 inches, while linear position resolution is 0.0169 inches, or 60 counts per inch. The range for material thickness is 0.01 to 0.75 inches. The linear position range is 0.25 to 82 inches. Further, in accordance with the physically realized embodiment, internal memory for a PDA was 192 MB ROM. An external memory with SD for back up was also provided. Storage on a network was provided through a PDA WiFi.

With respect to the user interface, a graphical user interface with an LCD display was used. Button-type enabling switches were utilized for various software functions. If desired, a software keypad can also be provided on the PDA screen, for purposes of identifying sheet coils. With respect to other specifications, all tolerances were met with an environment of up to 100 degrees Fahrenheit. Drop resistance was provided for up to 4 feet. In addition, the system 400 is preferably splash resistant.

Figures 31, 32:
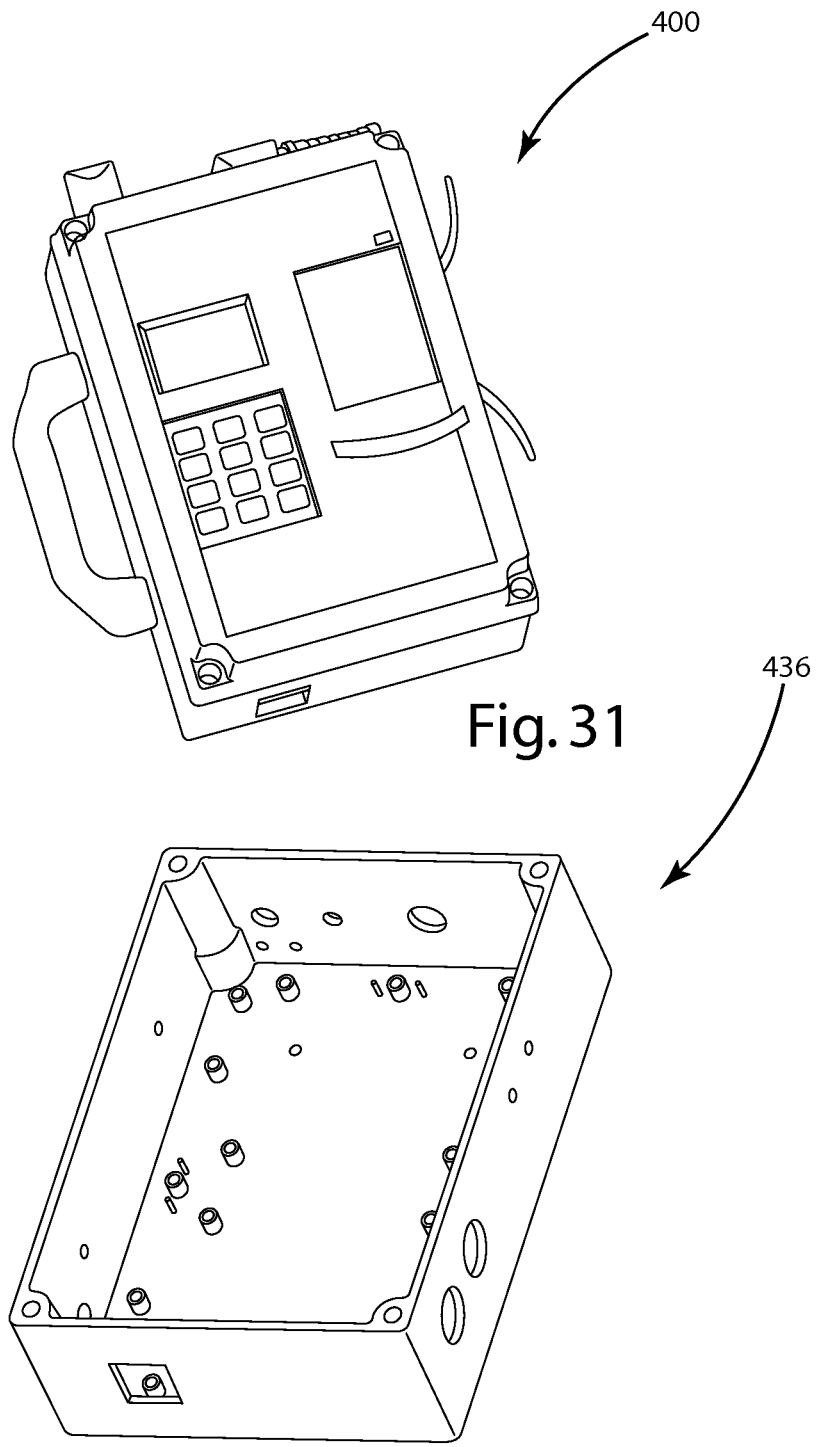
FIG. 31 is a perspective view of the case assembly of the gauge profile system illustrated in FIG. 29.
FIG. 32 is a perspective view of the case bottom of the case assembly shown in FIG. 31.

Turning specifically to FIGS. 29-44, the gauge profile system 400 has a configuration as particularly shown in FIGS. 29 and 31, in perspective view. The gauge profile system 400 includes a case cover 402 for protecting instrumentation within the severe environment. A PDA 404 is provided, which can be conventional and commercially available. An ultrasonic test 406 is also provided. The entirety of the profile system 400 or case assembly 400 also includes a rectangular-shaped top plate 408, with a cleat 410. A control board 412 is also provided, with electronics associated with the controller residing thereon. The profile system 400 also includes the wand handle 414. In addition to the foregoing, strain relief is provided by the strain relief device 416. Two power switches are provided, identified as power switches 418 and 424.

As earlier stated, the profile system 400 can be powered in part by internal batteries. The batteries are held through a top battery clamp 420 and a bottom battery clamp 426. In addition, for purposes of charging, a PDA charge connector 422 is also provided. For purposes of indicating proper operation, a power indicator light 428 is additionally provided. With respect to the strain relief 416, a roundabout 430 is also provided and secured to the strain relief device 416. As described in subsequent paragraphs herein, the gauge profile system 400 also includes a string encoder 432.

In addition to the previously described elements, the profile system 400 also includes a back plate 434. Magnets 438 are provided for purposes of releasably securing the profile system 400 to a stand or the like, while not in use. Also, the magnets 438 provide for a means of releasably securing the profile system 400 to the sheet coil 10 to be measured, during operation.

Figure 33:
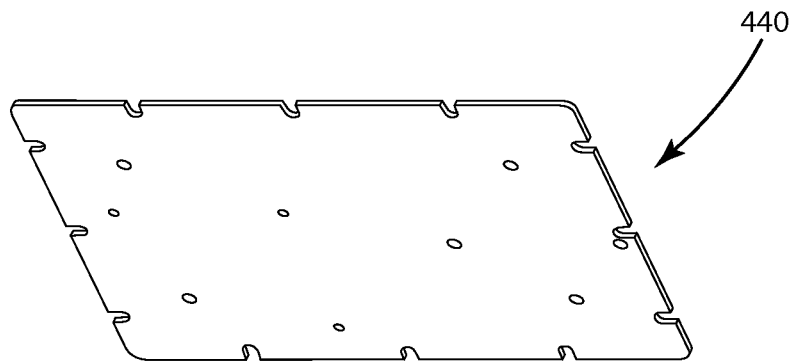
FIG. 33 is a perspective view of the case bottom plate of the case assembly shown in FIG. 31.
Figure 34:
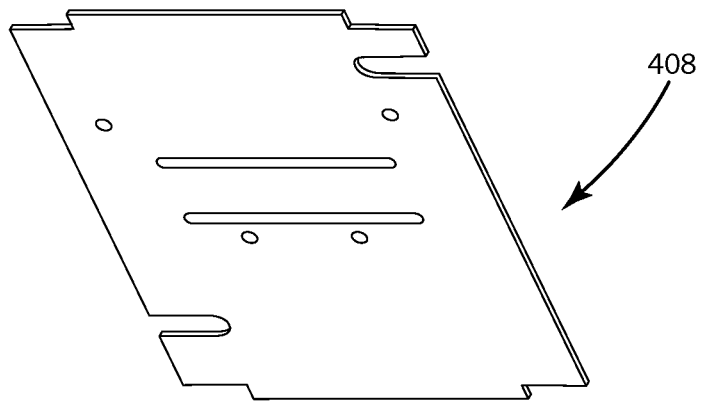
FIG. 34 is a perspective view of the case top plate of the case assembly shown in FIG. 31.
Figure 35:
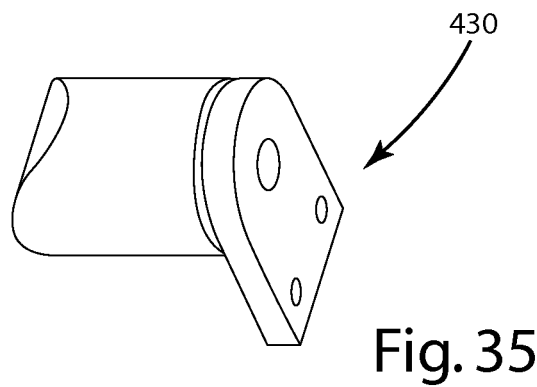
FIG. 35 is a partially perspective view of the roundabout of the case assembly shown in FIG. 29.
Figure 36:
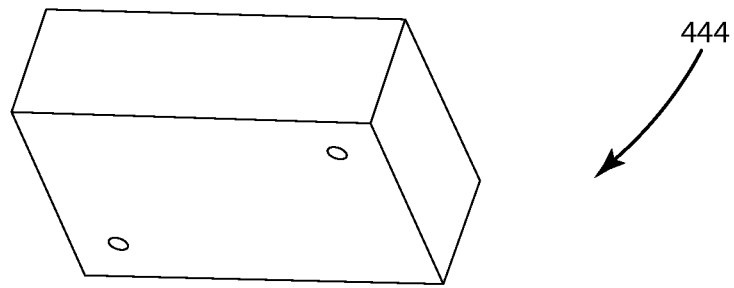
FIG. 36 is a perspective view of a PDA standoff of the case assembly shown in FIG. 29.
Figure 37:
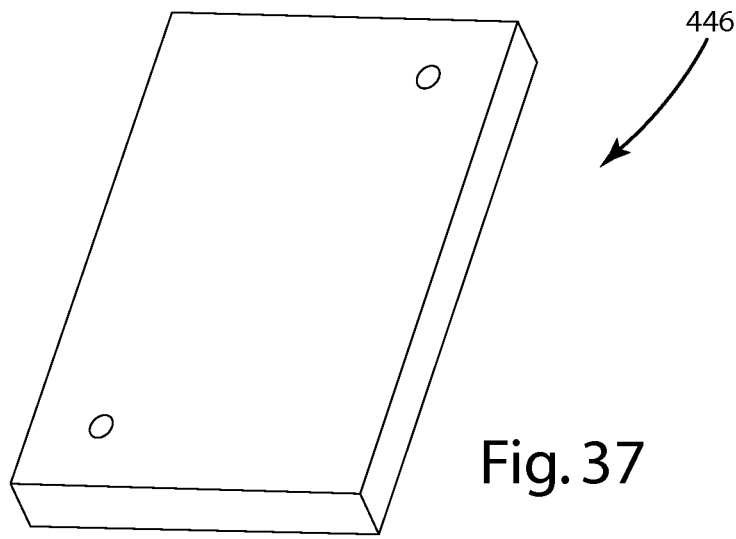
FIG. 37 is a perspective view of an Olympus standoff of the case assembly shown in FIG. 29.
Figure 38:
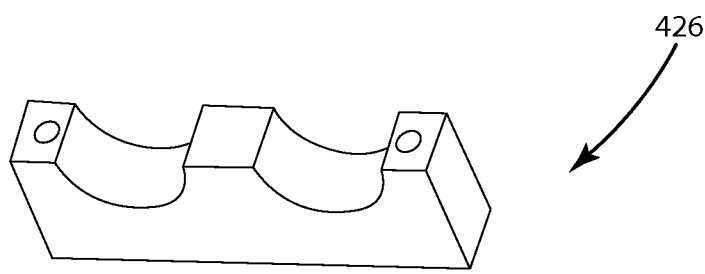
FIG. 38 is a perspective view of the battery bottom clamp of the case assembly shown in FIG. 29.
Figure 39:
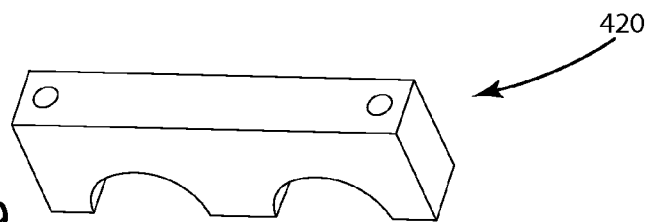
FIG. 39 is a perspective view of a battery top clamp of the case assembly shown in FIG. 29.
Figure 40:
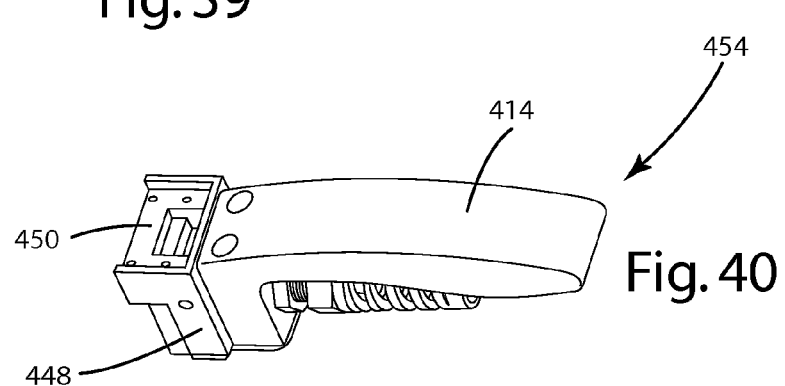
FIG. 40 is a perspective view of the wand assembly of the case assembly shown in FIG. 29.
Figure 41:
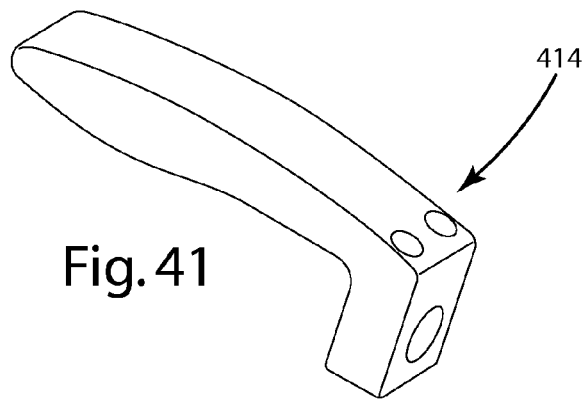
FIG. 41 is a perspective view of the wand handle of the wand assembly shown in FIG. 40.
Figure 42:
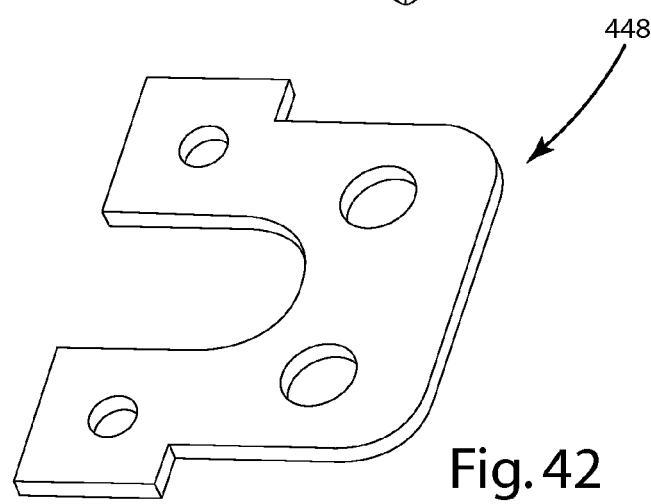
FIG. 42 is a perspective view of the wand bottom plate of the wand assembly shown in FIG. 40.
Figure 43:
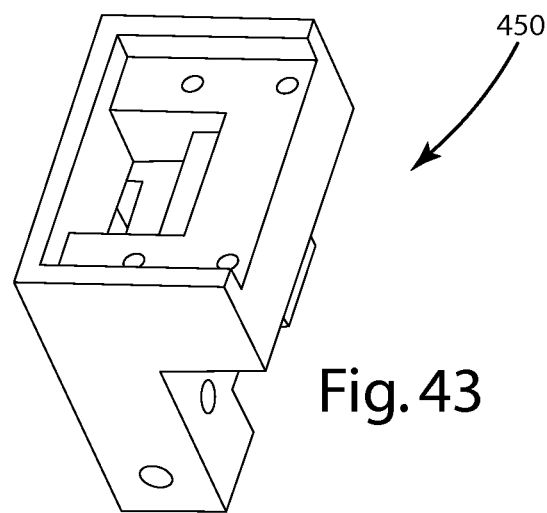
FIG. 43 is a perspective view of the wand main of the wand assembly shown in FIG. 40.
Figure 44:
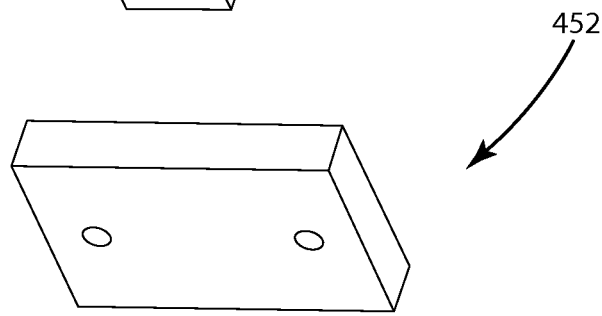
FIG. 44 is a perspective view of the wand cover of the wand assembly shown in FIG. 40.

The entirety of the profile system 400 or case assembly 400 is also shown in FIG. 31. FIG. 32 illustrates the case bottom 436. Correspondingly, FIG. 33 illustrates, in perspective format, the case bottom plate 440. The case top plate 408 and the case roundabout 430 are further illustrated in FIGS. 34 and 35, respectively. In addition, FIG. 36 illustrates a PDA standoff 444, while FIG. 37 illustrates an Olympus standoff 446. The bottom battery clamp 426 and the top battery clamp 420 are further illustrated in FIGS. 38 and 39, respectively. In addition to the foregoing, FIG. 40 illustrates the wand assembly 454, manually held by the operator during use of the gauge profile system 400. The wand assembly 454 includes the previously described wand handle 414. In addition, the wand assembly 454 includes the wand bottom plate illustrated in FIG. 42, the wand main 450 illustrated in FIG. 43, and the wand cover 452 illustrated in FIG. 44.

Figure 45:
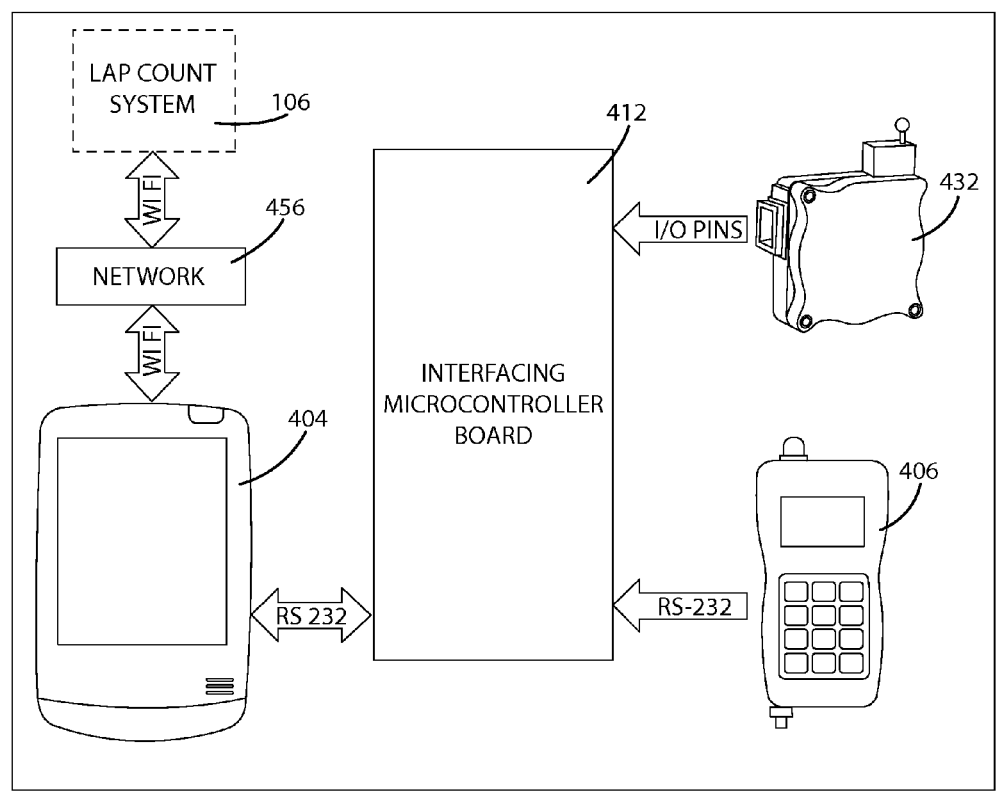
FIG. 45 is a partially schematic and partially diagrammatic illustration of the gauge profile system as utilized with the lap count system.

FIG. 45 is a diagrammatic view illustrating the functional and interconnected relationships among the lap count system 106, a network 456 and the various devices associated with the gauge profile system 400. Specifically, the lap count system 106 can correspond to the lap count system 106 previously described in detail herein with respect to the gauge profile apparatus 100. The network 456 can include any conventional network to which the appropriate data may be applied. A functional relationship between a gauge profile system and a lap count system was previously described herein and illustrated in FIG. 3. The functions performed by the system illustrated in FIG. 3, using the average lap gauge data from the lap count system 106 and the outside/inside lab profile data from the gauge profile system will also be utilized by the network 456 in the same manner. That is, the ultimate output desired through the use of the gauge profile apparatus using the gauge profile system 400 in accordance with the invention is an average three-dimensional profile over the length of a sheet coil 10. As with the gauge profile system 104 previously described herein, the gauge profile system 400 utilizes an ultrasonic gauge device (i.e., the ultrasonic tester 406) for purposes of bombarding the sheet coil material with high frequency sound waves. This information from the tester 406 is applied through an RS-232 interface to an interfacing microcontroller board 412. The RS-232 interface from the ultrasonic tester 406 to the microcontroller board 412 can have the following specifications: 19200 baud; 8 bits; 1 stop bit; no parity; and no flow control. Correspondingly, the PDA 404 has bidirectional communication with the interfacing microcontroller board 412. This communication is also provided through an RS-232 interface, which may have the same specifications as the interface between the ultrasonic tester 406 and the microcontroller board 412.

Correspondingly, the string encoder 432 can be utilized to connect to an encoder counter circuit (also on the microcontroller board 412) through a 3-channel (e.g., A, B, Z) quadrature interface. The encoder counter relays encoder counts to the serial interface circuit through the use of a 16 byte data bus. In addition to the foregoing, the PDA 404 may be utilized with the network 456, through bidirectional transmission between the network 456 and the PDA 404 using an 802.11b wireless connection to a main computer or the like for purposes of appropriate communications. A corresponding wireless connection can also be made so as to provide bidirectional communication between the lap count system 106 and the network 456. Again, it should be emphasized that the data being provided to the network 456 by the gauge profile system 400 corresponds to the same type of data generated by the gauge profile system 104 previously described herein with respect to the gauge profile apparatus 100.

In operation, the gauge profile system 400 will typically be used by sheet coil receiving personnel for purposes of gathering data to create a cross-section of the thickness of one layer of the steel coil 10 from the leading edge of the coil to the opposite edge. At the beginning of a day, the operator would likely remove the gauge profile system 400 from a charger, and enable power. Once powered, the gauge profile system 400 can be programmed so as to automatically be connected to a wireless area network associated with the operator's company. The gauge profile system 400 may then be programmed so as to either automatically download daily coil receiving information, or instruct the operator to download daily coil receiving information from the network 456.

Figure 46:
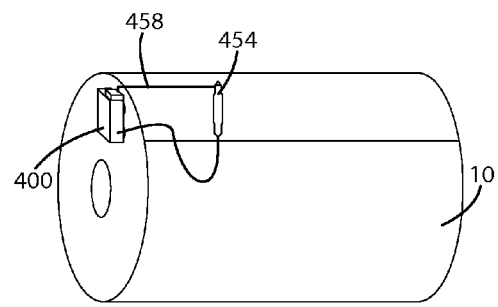
FIG. 46 is a simplified perspective view of the gauge profile system as it may be utilized with the sheet coil.
Figure 47:
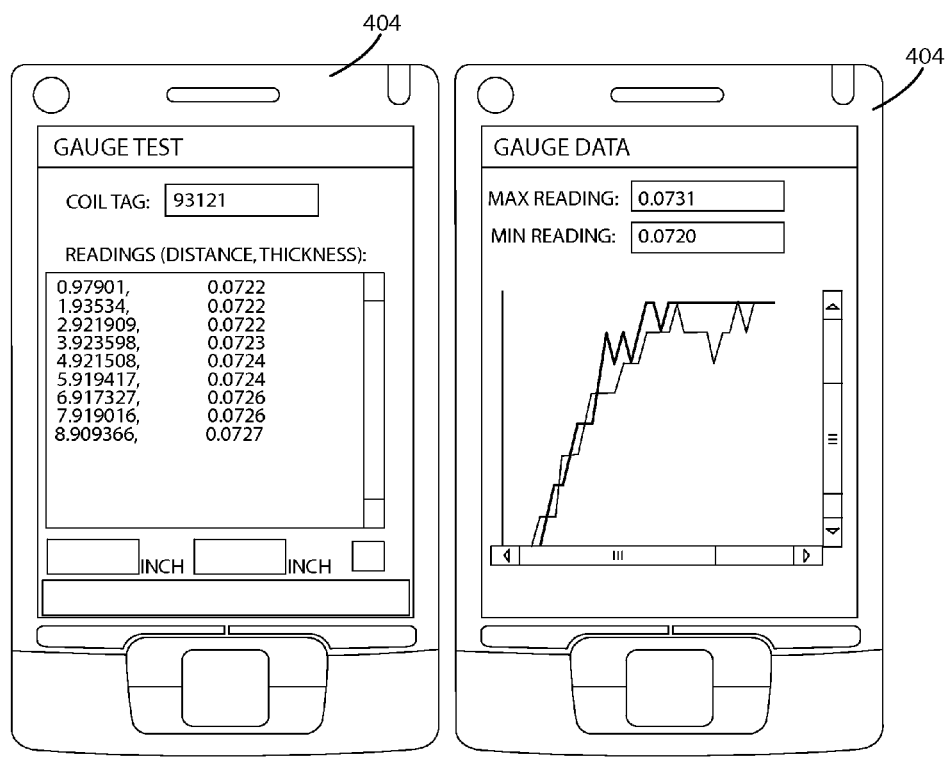
FIG. 47 shows a pair of images of the PDA of the gauge profile system, illustrating a simulated image file and data that will be saved.
Figure 48:
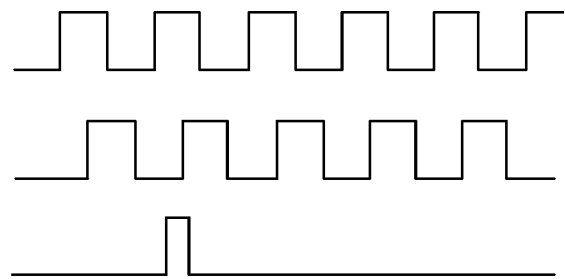
FIG. 48 is an illustration of the encoder signal structure which may be utilized with the string encoder of the gauge profile system.

When a sheet coil 10 is received, the operator may take the profile system 400 off of the charger and mount it to one side of the sheet coil 10 using the magnets 438 located on the back side of the case assembly. When the profile system 400 is mounted to the coil 10, the operator can then select the correct coil ID and measurement mode from drop down options associated with the PDA 404. When successfully completed, the operator can press the "gauge test" button, so as to begin triggering measurements to be stored in the PDA 404. When the operator is finished taking measurements, the operator can press a "done" button located in the software associated with the PDA 404. When the button is pressed, the PDA 404 will stop the measurement process, analyze the collected measurement data, and upload the data and analysis to a specified location on the network 456. When the gauge profile system 400 is not in use, it is preferably plugged into an appropriate charger. A sketch of the profile system 400 in use (absent the operator) is shown in FIG. 46. Simulated image file information and data that may be saved are illustrated in the representative screens of the PDAs 404 shown in FIG. 47.

The linear measurement provided by the gauge profile system 400 is achieved through the use of the string encoder 432. Such devices are commercially available. The underlying technology of the string encoder 432 is a rotary encoder utilizing three signals (i.e., A, B and Z). Signals A and B are generated 90 degrees out of phase so as to indicate direction, while signal Z acts as a "home pulse" (which indicates a full revolution). A shaft of the encoder 432 can be attached to a spool of stainless steel cable 458 illustrated in FIG. 46. As the cable 458 is unspoiled, the shaft of the encoder 432 rotates, and A/B channels are pulsed in quadrature (i.e., 90 degrees out of phase with respect to one another). Rising and falling edges of the channels A and B can be interpreted to increment (with the shaft turning clockwise) or decrement (with the shaft turning counter-clockwise) the total number of encoder counts. Channel Z is used to confirm the total number of counts. The encoder counts are interpreted as a linear position by multiplying the total number of counts by the encoder's resolution. The resolution is typically given in inches per count.

As earlier described, the gauge profile system 400 includes the PDA 404. An example and commercially available PDA which may be utilized as the PDA 404 is the HP iPaq Hx 2495 PDA. The PDA 404 acts as the major means of communication, storage and analysis for data collected about individual coils from the linear and ultrasonic measurement devices. The PDA 404 also acts as a user interface to the measurement sensors and data which are stored on the network 456. The operator can start a measurement from the PDA 404 by selecting the appropriate options and coil ID, and then pressing a software button "start." The device can then wait for serial data from the embedded device, which sends data in the format of "distance, thickness" where distance is a linear distance from the edge of the coil in encoder counts, and thickness is the thickness of the coil at the linear distance in inches where a measurement has been taken. After successful reception of data from the embedded device, the PDA 404 can respond with an "*" to indicate that it has successfully received and parsed the data. If data reception was unsuccessful, the PDA 404 can respond to the embedded system with an "X" so as to indicate that the data was not received correctly, and that the embedded device should resend the data. When the operator has completed coil measurements, the "end" button can be pressed, and the PDA 404 can send the "end" command to the embedded device, so as to let it know that it is no longer accepting measurement data. This function can also indicate to the PDA 404 to begin analysis of the data.

The data that has been collected can be compiled into a text file and a "line of best fit" can be computed. The line of best fit can be plotted with real data points, and saved as an image file. Accordingly, both the text file and the image of the plot can be uploaded to a specified location on the network for later review. An example set of equations for the "curve-best-fit" analysis is illustrated in FIG. 60, which also indicates the definitions of the variables.

The interface microcontroller board 412 can include two microcontrollers, associate control communications and encoder counting. The board 412 can also act as a means for powering the ultrasonic measurement device 406.

One of the microcontrollers can act as the interconnect between the PDA 404 and the measurement devices, as well as providing visual feedback to the user through the use of LEDs. This microcontroller can wait for a start command from the PDA 404, which can essentially notify the microcontroller to start the measurement process with or without interval measuring enabled. If the microcontroller receives a start command without interval measuring enabled, then it will wait for and relay valid measurements of distance and thickness to the PDA 404 without indicating when the operator should take the measurements. If the microcontroller receives the start command with interval measuring enabled, it will wait for and relay valid measurements of distance and thickness to the PDA 404, while indicating points at which the operator should take a measurement through use of different colored LEDs.

When the measurement process is initiated, the ultrasonic measurement from the tester 406 will continuously send thickness measurements at an approximate rate of 16 Hz. The microcontroller 412 can continuously parse this thickness data and determine validity. If valid, the thickness measurement is relayed along with the linear position to the PDA 404. This process will be repeated until the microcontroller receives an end command from the PDA 404.

The second microcontroller can function as an encoder counter, and may be clocked at a speed of 20 MHz, in order to count encoder pulses as fast as possible. As earlier described, the signals into this microcontroller from the string encoder 432 are signals A, B and Z. The A and B signals are square pulses, where B is 90 degrees out of phase from A (this is for purposes of determining if the string or cable 454 is being pulled out or retracted in). Signal Z is a home pulse to indicate that there has been one full resolution. The encoder counts are relayed from this microcontroller to the first microcontroller through a 16 byte data buss. A reset line comes from the first microcontroller and is used to reset the encoder count values.

The power supply circuit can include two subsystems. The first can be a solid state power multiplexer designed to switch between two possible power connections, namely USB buss power and batteries. The second subsystem can be a voltage regulator. Commercially available voltage regulators appropriate for these purposes are available from Linear Technologies. The regulator is configured in a SEPIC mode. This mode allows regulation of an input voltage, in the range of 3 to 7 volts, with the output voltage at 5 volts. The regulator is necessary, since the USB voltage can range both above and below 5 volts. The low battery indicator function of the regulator is set up so as to drive low when the input voltage drops below a particular threshold.

Serial interfacing can be provided at plus and minus 10 volt levels. A logical multiplexer can be used to split the data transmitted from the computing option. If the USB is connected, then the USB port will be a primary mode of communication. The interconnect board 412 will send data to both the serial port and the USB port. If the USB port is not plugged in, then the interconnect board will only receive data from the serial port.

The ultrasonic sensor 406 can use a delay line transducer with a dry couplant so as to take thickness measurements of one layer of the steel coil 10. The measurements can have a resolution of 0.0001 inch. The measuring device will send thickness data to the serial port at a predefined rate. The tester 406 essentially works by transmitting an ultrasonic sound wave through the target material, and analyzing the reflective wave to determine the thickness. This concept of transmitting ultrasonic sound waves and appropriate means for analysis to determine thickness were previously described herein with respect to the gauge profile system 104.

Figure 49:
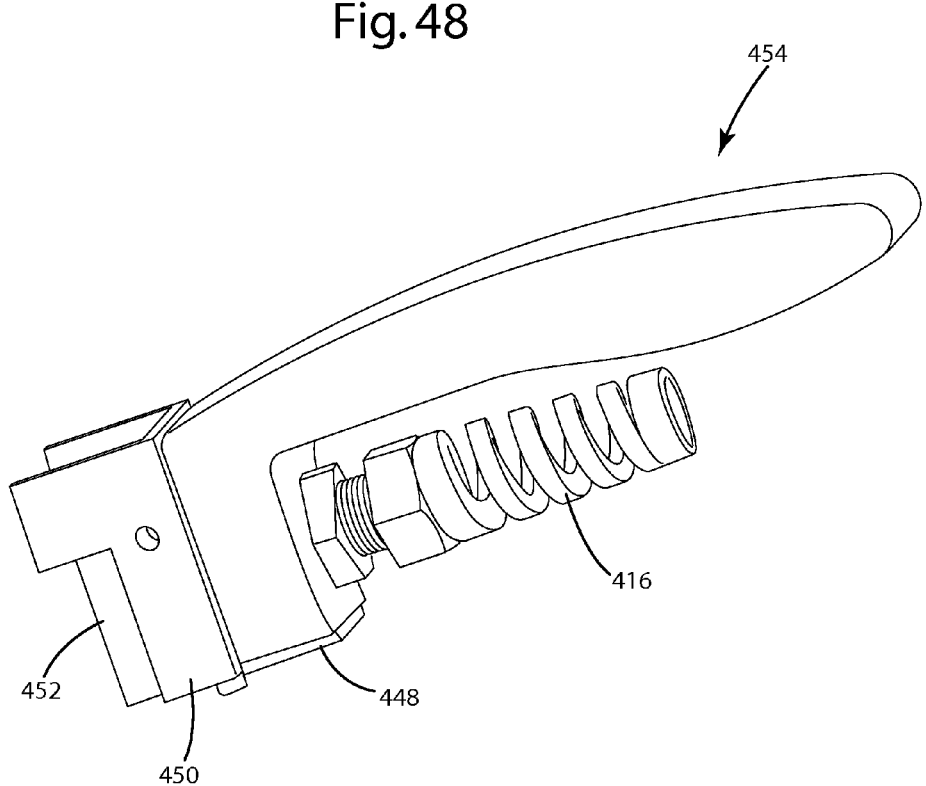
FIG. 49 is a perspective view of the transducer wand utilized with the gauge profile system.
Figure 50:
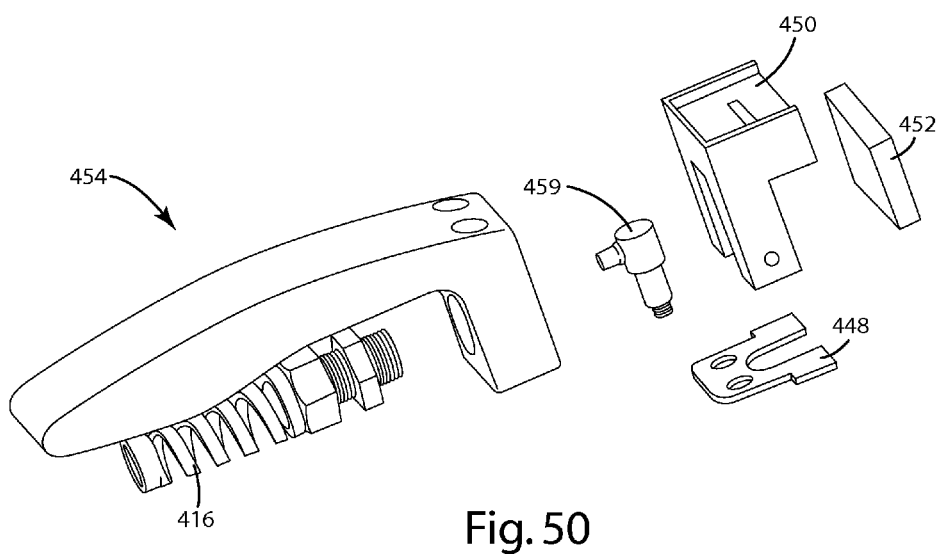
FIG. 50 is an exploded view of the wand assembly for the gauge profile system, showing various components of the wand assembly as previously illustrated in individual illustrations.

For purposes of further description and detail, the wand assembly 454 is further shown in FIG. 49. The wand assembly 454 is also shown in an exploded view in FIG. 50. FIG. 50 illustrates the wand base or bottom plate 448, main 450, cover 452, delay line transducer 459 and the strain relief 416.

Figure 51:
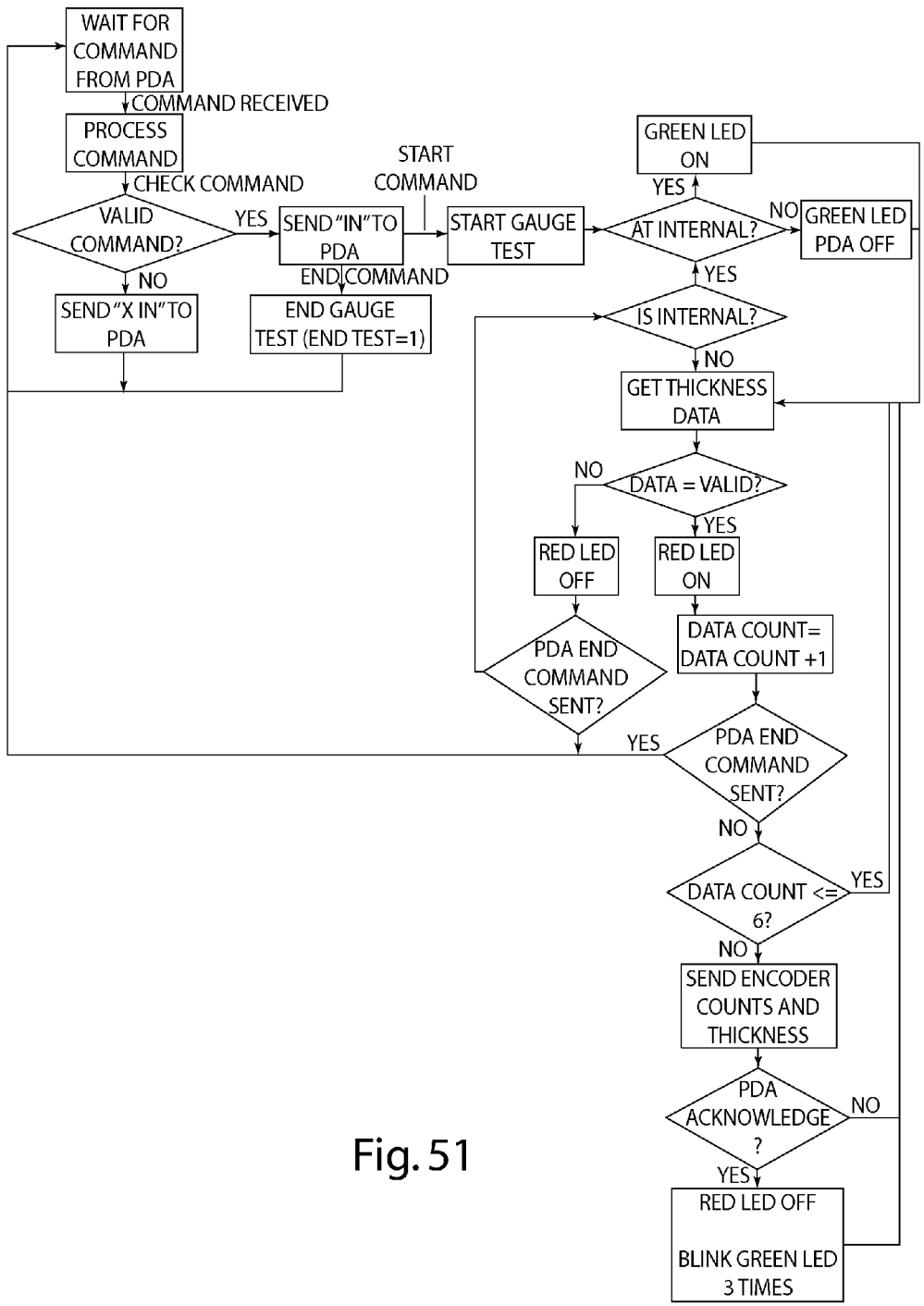
FIG. 51 is a block diagram illustrating a functional sequence for the serial relay controller.
Figure 52:
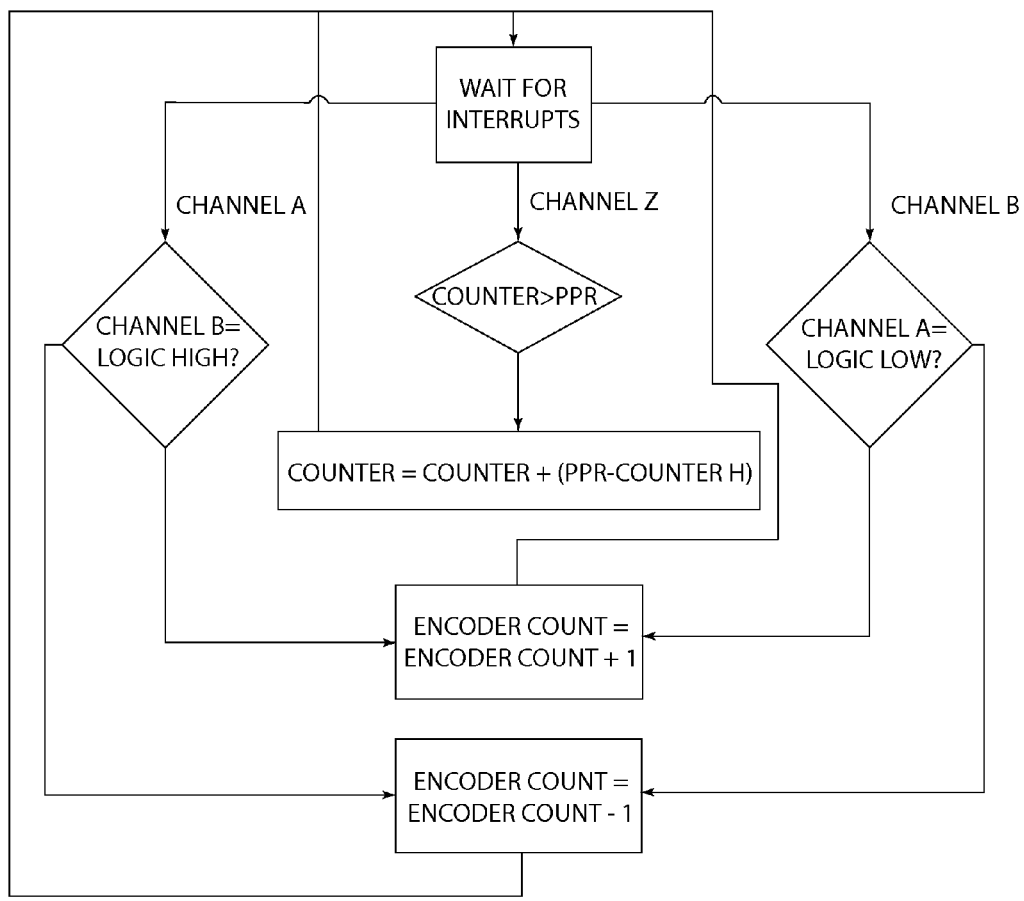
FIG. 52 is a block diagram showing functional steps associated with the encoder count controller.

FIG. 51 illustrates a block diagram for the serial relay controller. The diagram is essentially self-explanatory. The controller essentially waits for a command from the PDA 404. When received, the command is processed so as to determine validity. If the command is a start command, the gauge test is initiated and thickness data and data counts are received and determined. More specifically, thickness data and data counts are continued until end signals are received. Correspondingly, FIG. 52 is a block diagram for the end counter count controller. The diagram is self explanatory, and essentially provides the functions of sequentially making counts and determining when the counting process should end.

Figure 53:
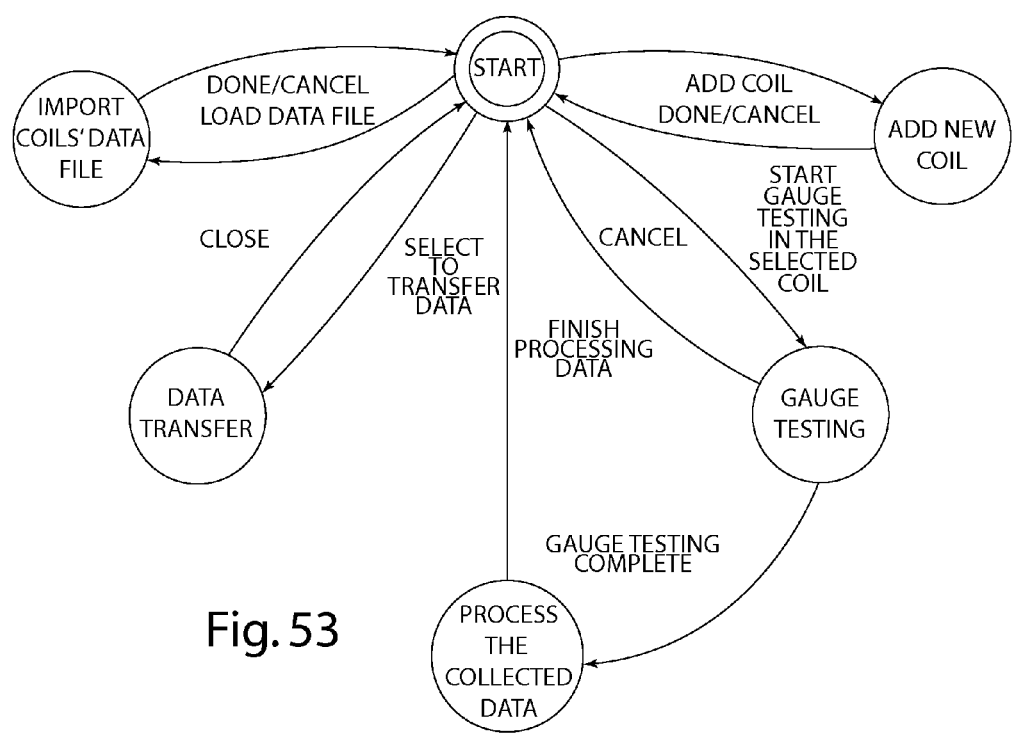
FIG. 53 is a functional state diagram of the software utilized with the PDA for the gauge profile system.
Figure 54:
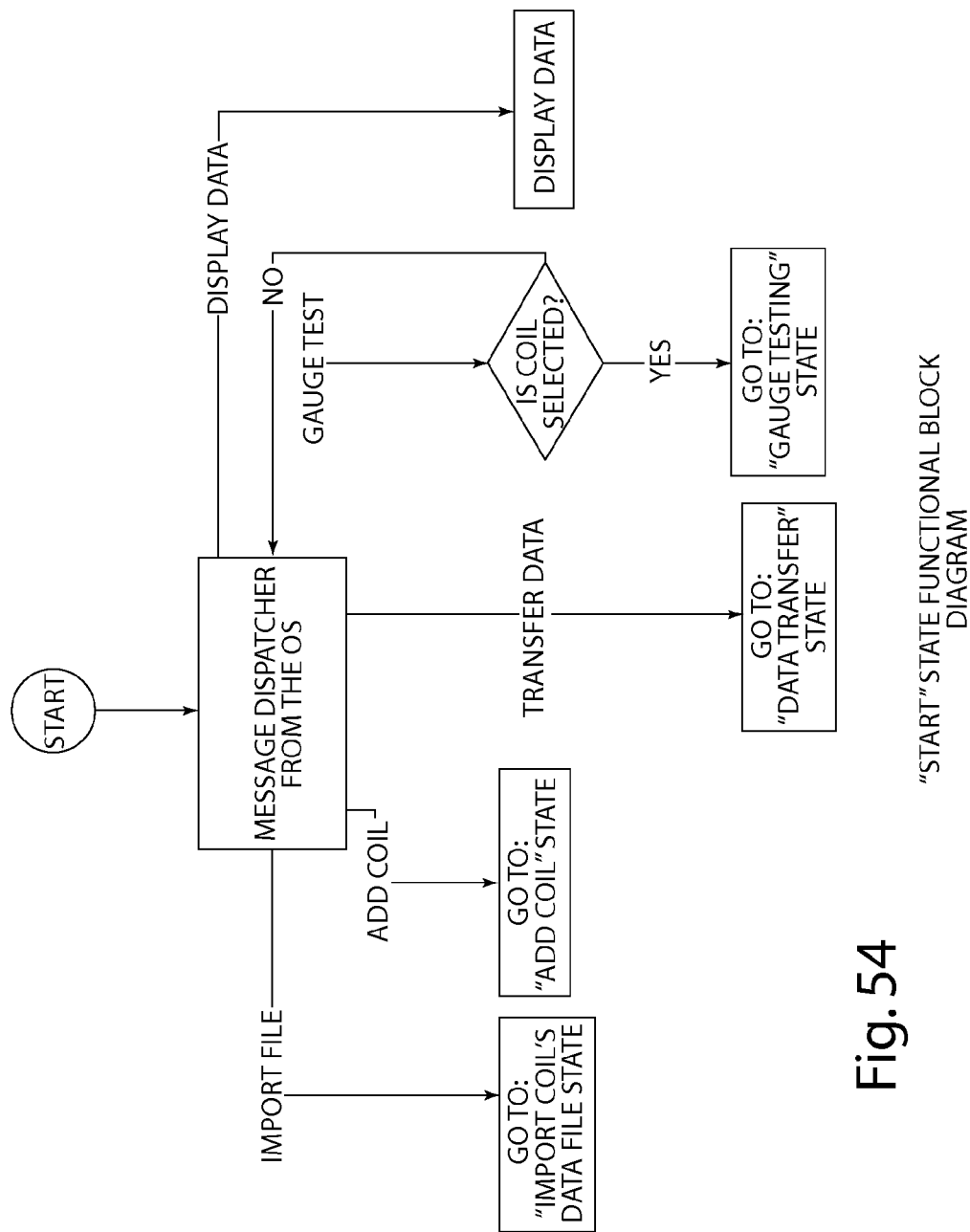
FIG. 54 is a state functional block diagram illustrating the "start" state.
Figure 55:
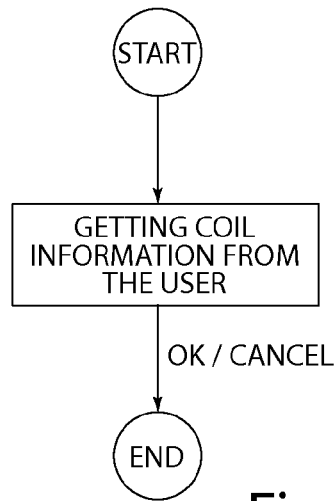
FIG. 55 is a state functional block diagram illustrating the "add coil" state.

FIG. 53 is a functional state diagram of the PDA software which will be incorporated within the PDA 404. Again, it is believed that this state diagram is self explanatory, but will be set forth in greater detail in subsequent illustrations herein. Essentially, following an initiation or start of the process, function states include the addition of a new sheet coil 10, gauge testing, processing of collected data, data transfer and the importation of data files associated with the sheet coils 10. FIG. 54 illustrates a state functional block diagram for the start command. Essentially, a screen is displayed for the operator, so as to indicate start up. Software information is then further displayed, along with tags lists for the sheet coils. The operator may add additional tags and then initiate testing. The state will also allow the operator to visualize the plots of the collected tests and the overall results. FIG. 55 is a state functional block diagram for the "add new coil" state. In this state, the coils information form that the operator must fill out is displayed. If the operator does not discard or otherwise cancel the operation, the input information is added to the database, and the list of selectable coils is updated.

Figure 56:
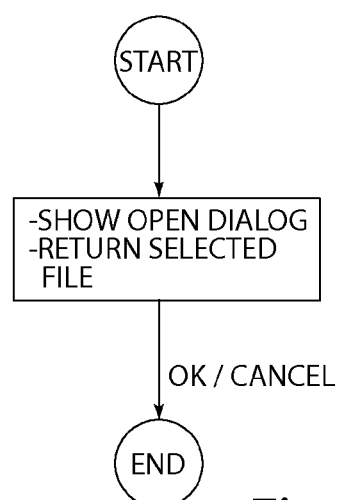
FIG. 56 is a state functional block diagram showing the "import coils data file" state.

FIG. 56 illustrates a state functional block diagram for the "input coils data file" state. This state allows the operator to add a list of coils from the file. Again, if the operator does not cancel the operation, the input information is put into the database and the list of selectable coils is updated.

Figure 57:
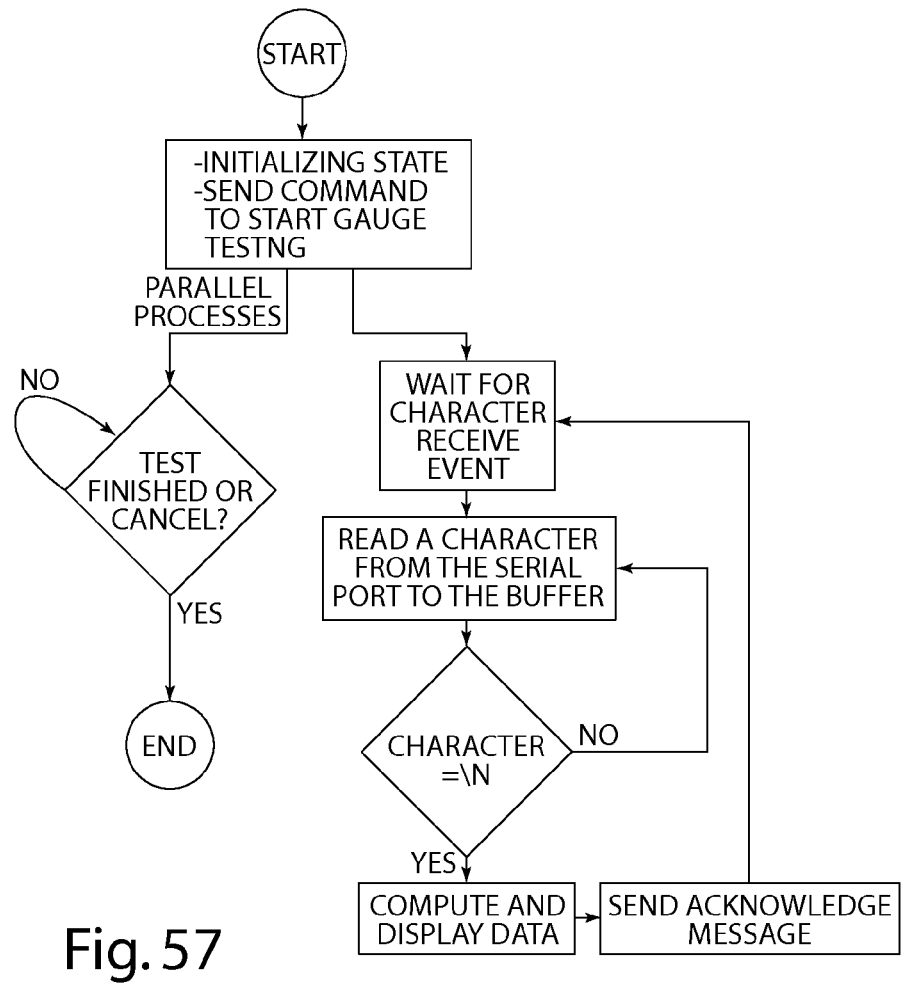
FIG. 57 is a state functional block diagram illustrating the "gauge testing" state.
Figure 58:
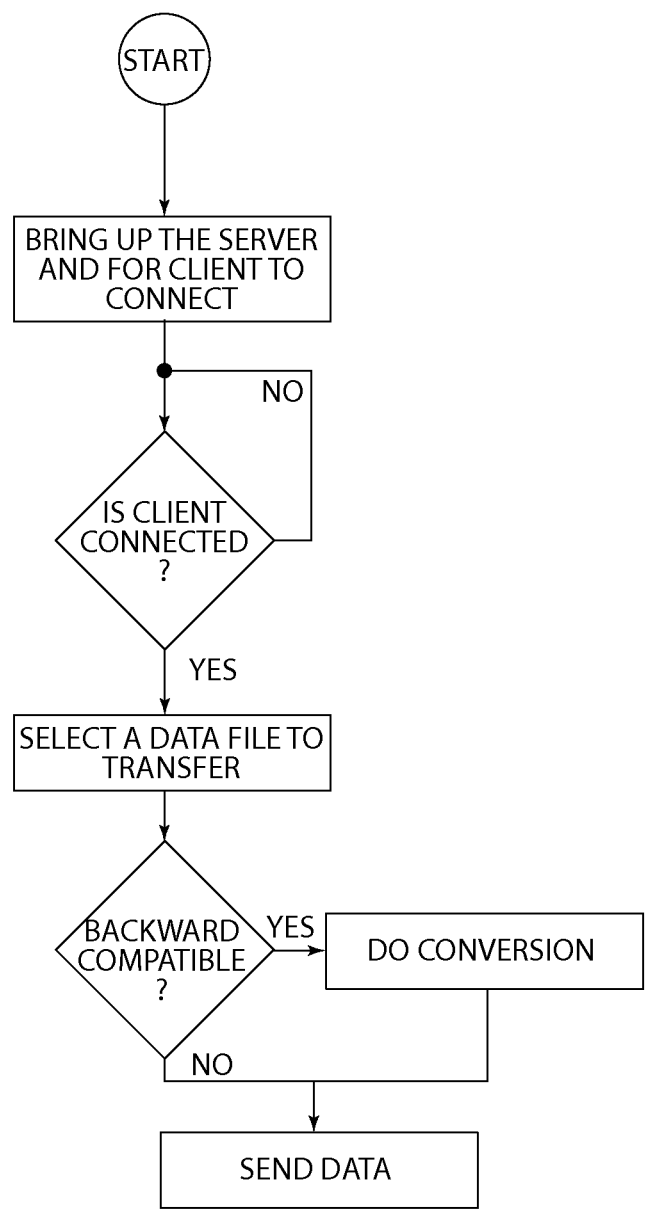
FIG. 58 is a state functional block diagram showing the "data transfer" state.

FIG. 57 illustrates a state functional block diagram for the "gauge testing" state. In this state, serial commands are transmitted to the appropriate microcontrollers so as to initiate the gauge test for the selected coil. A "listen" operation is then performed on the serial port, so as to retrieve the distance and thickness measurement. If the operator cancels the test, the test is stopped and the results are discarded. If the operator finishes the test, the measurements are appropriately stored. FIG. 58 is a state functional block diagram for the "data transfer" functions. In this state, a TCP server is established, to which data is to be transferred. The operator then selects a data file, and the data file is transferred to the connected client. Correspondingly, FIG. 59 is a state functional block diagram illustrating the "process the collected data" state. In this state, a computation is made of the "best-fit" value. The data is then plotted and stored.

In accordance with all of the foregoing, a second embodiment of a gauge profile system 400 has been described and illustrated herein. Advantageously, the gauge profile system 400 can operate with only one operator. Further, the gauge profile system 400 has relatively few moving parts. Also, the profile system 400 is relatively compact, thereby reducing the probability of damage when used in relatively severe environments.

It will be apparent to those skilled in the pertinent arts that other embodiments of gauge profile systems in accordance with the invention can be designed. That is, the principles of systems in accordance with the invention are not limited to the specific embodiments described herein. Accordingly, it will be apparent to those skilled in the art that modifications and other variations of the above-described illustrative embodiments of the invention may be effected without departing from the spirit and scope of the novel concepts of the invention.

What is claimed:

1. A gauge profile apparatus adapted for use with a sheet coil for determining an average three-dimensional profile over the length of the coil, said profile apparatus comprising:
   a gauge profile system for determining the relative distribution of material of said sheet coil for a cross-section of said material, said gauge profile system comprising:
      a linear slide comprising an end block having a reversal block mounted therein, with an upper belt arm and a lower belt and slide arm, said upper belt arm and slide arm being spaced apart and parallel to each other;
      said linear slide further includes an end clamp which clamps said linear slide to one end of said sheet coil, with a second clamp characterized as an adjacent clamp being utilized to clamp said linear slide to another edge of said sheet coil;
      a thickness sensor mounted to said lower belt and slide arm, said thickness sensor bombarding said sheet coil with high frequency sound waves, and with timing between echoes translated into distance determinations between top and bottom surfaces for said sheet coil, with said linear slide providing means for permitting traverse of said thickness sensor across a width of said sheet coil, while capturing thickness measurements during traversal;
      a control box mounted to an end of said linear slide, containing both mechanical and electronic elements for said gauge profile system, said control box being mounted to said adjacent clamp, and with power for said control box being provided as AC power through a power cord;
      signals transmitted between a desktop computer and said control box through an antenna, for purposes of providing control through said desktop computer;
      said control box further comprises a driver belt system having a drive pulley with a stepper motor belt positioned on said pulley, and with said pulley attached to a drive axle;
      said internal components of said control box further include a stepper motor having operating parameters comprising functional operation at low speed and for low torque applications, and further with said stepper motor having relatively high accuracy and high resolution characteristics;
      said control box further comprises an encoder receiving signals from said stepper motor which are digitally encoded and applied as input to a microcontroller, said encoder signals being applied as said digital input signals consisting of various motor characteristics, including position information for said microcontroller;
      said microcontroller applies said digital signals as input signals to said stepper motor driver for operating said stepper motor and causing said thickness sensor to traverse said sheet coil;
      said gauge profile system further comprises limit switches which are located outside of said control box and positioned adjacent said clamps, said limit switches operate so as to limit traversal of said thickness sensor along said lower belt and slide arm;
      said limit switches, when actuated by certain positions of said thickness sensor, operates so as to apply digital input signals to said microcontroller;
      said microcontroller functions so as to be responsive to said digital signals from said limit switches to generate digital signals applied to said stepper motor driver, so as to control stepper motor movement;
      said gauge profile system, within said control box, further comprises a wireless board, with serial digital signals applied in a bi-directional manner between said microcontroller and said wireless board, said wireless board being further functional so as to transmit and receive signals on lines attached to said antenna for purposes of transmission/reception of signals to remotely located computers; and
   a lap count system comprising an ultrasonic distance sensor and camera, for determining the average thickness of said sheet coil, through counting of a number of laps of said sheet coil and making a determination of an outside diameter of said sheet coil and an inside diameter of said sheet coil.

* * * * *